United States Patent [19]

Hwang et al.

[11] Patent Number: 5,312,837
[45] Date of Patent: May 17, 1994

[54] METHOD OF TREATING VIRAL INFECTIONS WITH ARYL MACROCYCLIC COMPOUNDS

[75] Inventors: Kou M. Hwang, Danville; You M. Qi, Redwood City; Su-Ying Liu, Belmont, all of Calif.

[73] Assignee: Genelabs Technologies, Inc., Redwood City, Calif.

[21] Appl. No.: 791,920

[22] Filed: Nov. 13, 1991

Related U.S. Application Data

[63] Continuation-in-part of Ser. No. 647,720, Jan. 29, 1991, Pat. No. 5,196,452, which is a continuation-in-part of Ser. No. 647,469, Jan. 29, 1991, Pat. No. 5,166,173.

[51] Int. Cl.$^5$ ............................................. A61K 31/185
[52] U.S. Cl. ...................................... 514/577; 514/602
[58] Field of Search ................................ 514/577, 602

[56] References Cited

U.S. PATENT DOCUMENTS 4,604,404  8/1986  Munson, Jr. et al. ............... 514/494

FOREIGN PATENT DOCUMENTS

0354818A2  8/1989  European Pat. Off.
0467185A2  7/1991  European Pat. Off.
61-83156   4/1986  Japan.
WO90/00596 1/1990  PCT Int'l Appl.
WO91/07183 5/1991  PCT Int'l Appl.
721103    11/1978  U.S.S.R.

OTHER PUBLICATIONS

Akerfeldt, S., et al., J. Med. Chem. 14(7):596–600 (1971).
Grollman, A. P., and Horwitz, S. B., in Drug Design (E. J. Ariens, ed.) vol. II, Chapter 7, pp. 261–272, Academic Press (1971).
Poh, B.-L., et al., Tetrahedron Letters 30(8):1005–1008 (1989).
Poh, B.-L., et al., Tetrahedron 46(12):4379–4386 (1990).
Poh, B.-L., and Lim, C. S., Tetrahedron 46(10:3651–3658 (1990).
Shinkai, S., et al., "Selective adsorption of uranyl ion ($UO_2^{2+}$) to a polymer resin immobiizing calixarene-based uranophiles," abstract from Chem. Abst. 109:35 (1988).
Shinkai, S., et al., "Synthesis and inclusion properties of neutral water-soluble calixarene," abstract from Chem. Abst. 113:666 (1990).
Shinkai, S., et al., "New Syntheses of Calixarene-p-sulphonates and p-Nitrocalixarenes," J. Chem. Soc. Perkin Trans. I:2297–2299 (1987).
Shinkai, S., et al., "Hexasulfonated Calix[6]arene Derivatives: A New Class of Catalysts, Surfactants, and Host Molecules," J. Am. Chem. Soc. 108:2409–2416 (1986).
Shinkai, S., et al., "New Water-Soluble Host Molecules Derived From Calix[6]arene," Tetra. Letters 25(46):5315–5318 (1984).
Akerfeldt et al. 75 CA:72945h 1971.

*Primary Examiner*—Frederick E. Waddell
*Assistant Examiner*—Russell Travers
*Attorney, Agent, or Firm*—Peter J. Dehlinger

[57] ABSTRACT

A method for inhibiting cell infection by an enveloped virus, by administering to an infection site, a therapeutically effective amount of a macrocyclic compound composed of aryl ring subunits connected one to another by ring-attached bridge linkages, and containing sulfonic acid-derived substituents carried on non-bridge atoms of the subunits.

8 Claims, 11 Drawing Sheets

Fig. 1
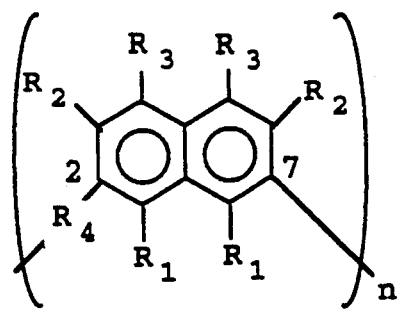
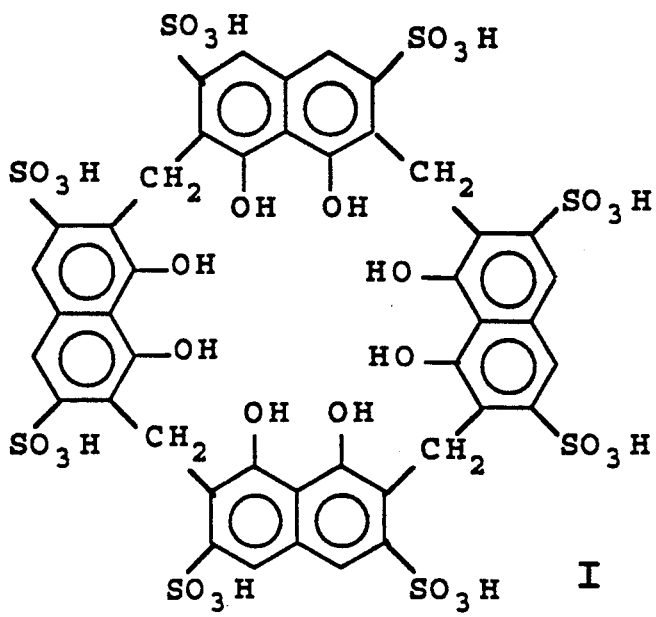
Fig. 2A
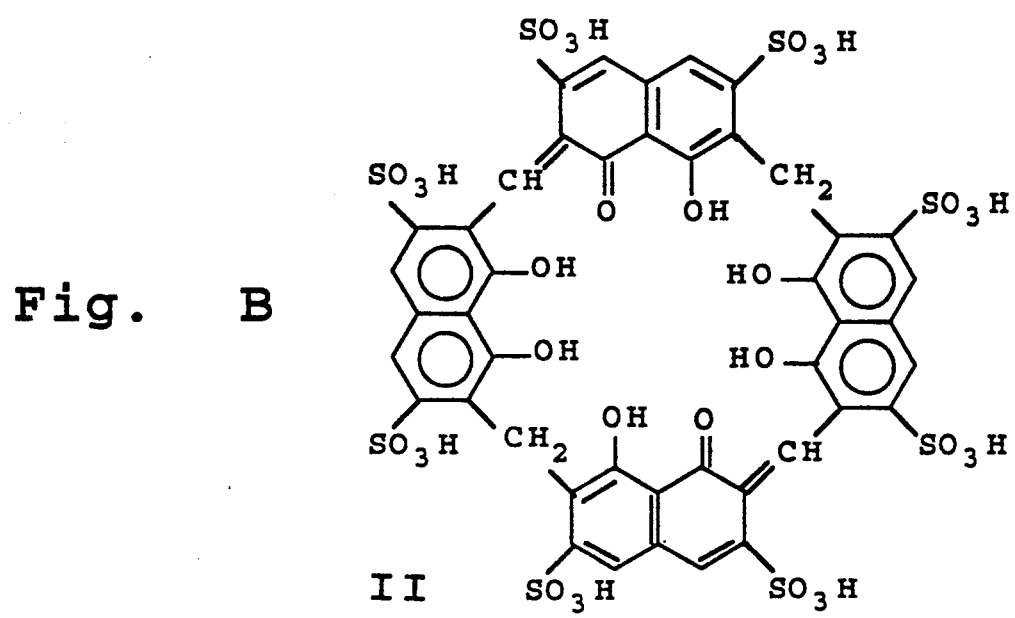
Fig. B

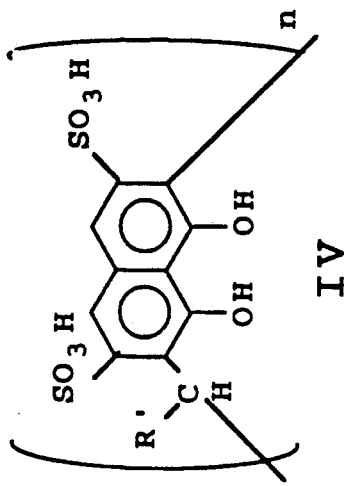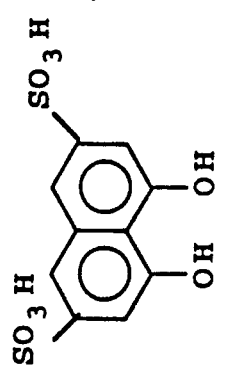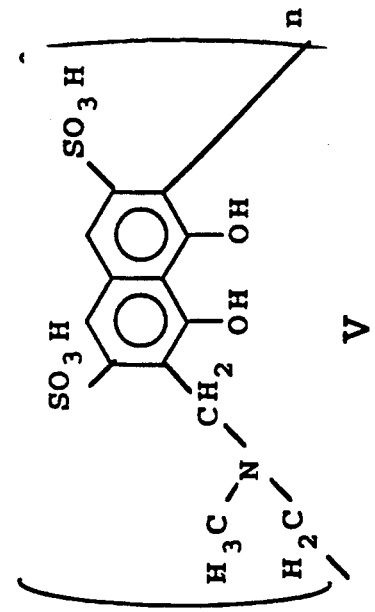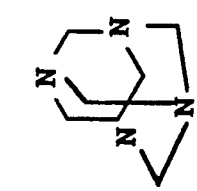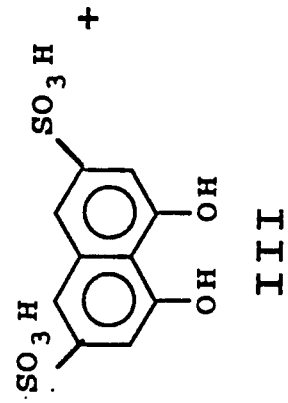
Fig. 3A
Fig. 3B

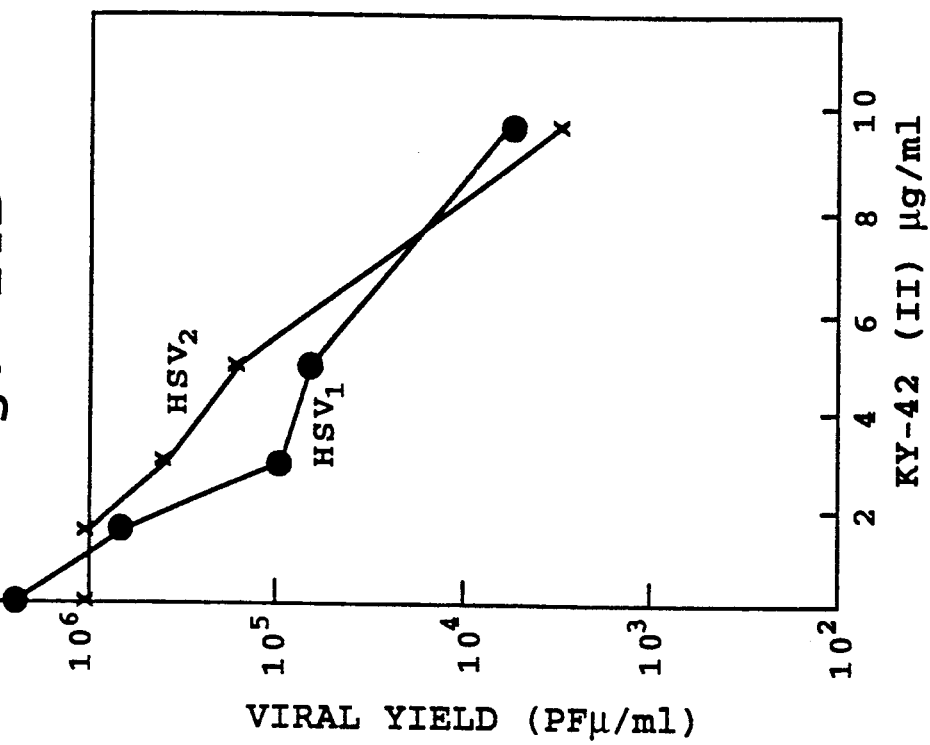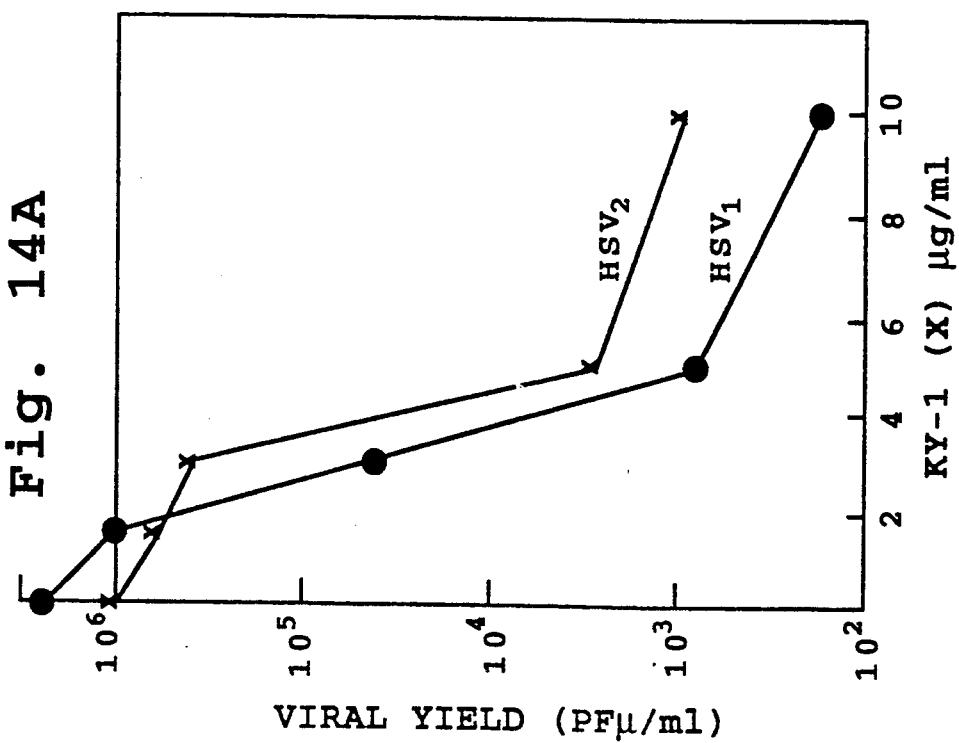

METHOD OF TREATING VIRAL INFECTIONS WITH ARYL MACROCYCLIC COMPOUNDS

This invention is a continuation-in-part of U.S. patent applications for "Macrocyclic Anti-Viral Compound ad Method", Ser. No. 647,720, now U.S. Pat. No. 5,196,452 and "Method of Treating Herpes Simpolex Virus Infection, Ser. No. 647, 469, now U.S. Pat. No. 5,166,173 both filed Jan. 29, 1991.

FIELD OF THE INVENTION

The present invention relates to a method for inhibiting cell infection by enveloped viruses.

REFERENCES

Barre-Simoussi, F., et al., Science 220:868–871 (1983).
Chanock, R. M., et al., AM. J. Hyg. 66:29–300 (1957).
Dick, E. C., Proc. Soc. Exp. Biol. Med. 127:1079–1081 (1968).
Erlich, K. S. , et al. , N. Eng. J. Med. 320:293–296 (1989).
Elion, G. B., et al., Proc. Natl. Acad. Sci USA 74:5617–5620 (1977).
Gibrack, C. D., et al., i. Inf. Dis. 146:673–682 (1982).
Gottlieb, M. S. , et al. , N. Eng. J. Med. 305:425–3 (1981).
Hansch, C. in Drug Design (E. J. Ariens, ed.), Vol. II, p. 271, Academic Press, (1971).
Hansch, C., Leo, A., Structure-Activity Correlation, Wiley, (1979).
Hilleman, M. R., Proc. Soc. Exp. Biol. Med. 85:183–188 (1954).
Huttunen, p., et al, *Pharmacol Biochem & Behav* 24:1733–38 (1986).
Jaffe, *Chem. Rev.*, 53, 191 (1953).
Kern, E. R., Amer. J. Med. 73:100–108 (1982).
Klatzmann, D., et al., Science 225:59–63 (1984).
Lifson, J. D., et al., Science 241:712–716 (1988).
March, J., Advanced Organic Chemistry 3rd ed., Chapter 9, Wiley (1985).
Mertz, G. J., et al., JAMA 260:201–206 (1988).
Mitsuya, M., et al., Proc. Natl. Acad. Sci.: 82:7096–7100, USA (1985).
Po, B-L, et al., Tetrahedron Letters, 30(8):1005 (1989).
Po, B-L, et al., Tetrahedron, 46(10):3651 (1990).
Po, B-L, et al., Tetrahedron, 46(12):4379 (1990).
Popovic, M., et al. Science 224:497–500 (1984).
Roizman, B., et al, Inter. Virol. 16:201–217 (1981).
Roizman, B., et al, J. Virol. 15:75–79 (1961).
Rowe, W. P., et al., Proc. Soc. Exp. Biol. Med. 84:570–573 (953).
Smith, R. A., et al., "Ribavirin: A broad spectrum antiviral agent: In: Stapleton, T., Editor, Studies With a Broad Spectrum Antiviral Agent. International Congress and Symposium Service (London), Royal Society of Medicine, 3–23 (1986).
Spear, P. G. [Roizman, B., Editor], The Herpes Simplex Viruses, Vol. 3, Plenum Press, New York, pp. 315–356 (1989).
Stannard, L. M. , et al., J. Gen. Virol. 68:715–725 (1987).

BACKGROUND OF THE INVENTION

The challenge in developing an effective therapy and prophylaxis for viral disease is to achieve inhibition of viral processes without producing extreme side effects and preferably without inducing viral resistance. Since viral replication requires use of the cellular apparatus of the host, treating virus infection by inhibiting viral replication can be lethal to the infected host cells as well. Ideally, the virus should be destroyed or inactivated in the host prior to its invasion of host cells. This is normally accomplished, with varying degrees of success, by the host's immune system, but this mechanism requires an earlier immune response, either by a prior infection or by vaccination. Further, many viruses, such as Herpes Simplex viruses (HSV) are able to effectively elude a host's immune systems, and at least one virus, the human immunodeficiency virus (HIV) is known to cripple the host's immune system (Gottlieb).

Currently, the most widely used anti-viral agents are nucleoside analogs. This class of drugs acts by disrupting viral replication, either by inhibiting enzymes required for nucleic acid processing, or by producing defective viral genomes, such as by premature termination of replication. As an example, acyclovir, a purine analog used in treating a variety of viral diseases, including herpes simplex virus-1 (HSV-1) and herpes simplex virus-2 (HSV-2) inhibits viral replication at several key points, including inhibition of viral thymidine kinase and DNA polymerase, and DNA strand elongation (Elion). Ribavirin, another purine analog, is the drug of choice in treating respiratory syncytial viruses (RSV) infection. This compound appears to act by reducing cellular GTP levels, blocking the action of several GTP-dependent viral processes (Smith). To date, the most common drug treatment of HIV infection is with zidovudine (Azidothymidine; AZT), a thymidine analog which is particularly effective against human retroviruses. AZT acts with high affinity to block viral RNA-dependent DNA polymerase (reverse transcriptase), but does also block human DNA- polymerase and causes chain termination (Mitsuya).

Other nucleic acid analogs include ganciclovir, vidarabine, idoxuridine, trif luridine and foscarnet (an inorganic phosphate analog). As indicated above, all of these drugs, by blocking viral replication, also have the capacity to disrupt and normal host replication and/or DNA transcription processes as well.

Understanding of the mechanisms of infection and replication of viruses has lead to alternate drug therapies, including attempts to block viral entry into cells, alter protein synthesis at the host ribosomes, complexation of viral DNA/RNA, and immunomodulation. Interferons are glycoproteins which have complex actions including enhancement of certain immune responses as well as direct antiviral action. They are more competent in preventing infection, rather than treating established viral infection, and their use leads to undesirable problems including acute, serious discomfort, bone marrow suppression, viral resistance, and development of host immune response to the interferon.

Treatment with "anti-sense" polymers of nucleic acids is a method in which the particular viral genome is the select target. The treatment provides a highly discriminating approach which would be expected to have minimal side-effects; its use as a therapeutic is hampered by problems of targeting, introduction into cells, and the quantity of material that would be required to block each strand produced. Agents which bind to and interfere with host ribosomal protein synthesis will block viral replication. These include the toxin ricin, various plant proteins such as pokeweed anti-viral protein, alpha sarcin, and other low molecular weight compounds. The weakness with the use of these materials is their lack of selectivity. In the treatment of HIV, additional therapy has been developed by specifically targeting the unique retroviral enzyme, reverse transcriptase. Non-retroviral systems do not produce or use this enzyme, but the virus cannot replicate without it.

In some instances, understanding of structural aspects of the mechanisms of replication of viruses has provided additional drug therapies. Certain viruses, including orthomyxoviruses and paramyxovirus, herpes viruses, togaviruses and retroviruses, contain a viral envelope which surrounds the viral capsid and nucleic acid. During cell infection by an enveloped virus, the plasma membrane of the host cell is altered to include some viral-coded proteins and, as the viral nucleoprotein core exits the host cell in which it was assembled, it becomes enveloped with the modified membrane, thus forming the viral envelop. Because this structure is unique to host cells when they are virally infectious and distinct from normal cells, it can serve as an additional target for therapeutic assault.

SUMMARY OF THE INVENTION

The present invention provides a method for inhibiting cell infection by enveloped viruses. The method involves exposing the cells to a macrocyclic compound composed of aryl ring subunits connected one to another by ring-attached bridge linkages which form a continuous chain of connected backbone atoms. The subunits have sulfonic acid-derived substituents on non-backbone atoms of the aryl subunit rings.

The ring subunits preferably include naphthalene subunits with sulfonic-acid derived substituents at the 3 and 6 ring positions, phenyl subunits with sulfonic acid-derived substituents at the 4 ring position, where the bridge linkages in the macrocycle are between the 2 ring-carbon position of one naphthalene or phenyl group, and the 7 ring-carbon group of an adjacent naphthalene group or 6 ring-carbon position of an adjacent phenyl group. The compound preferably includes 4–8 such subunits. The sulfonic acid-derived substituent is preferably sulfonic acid, a sulfonate salt, sulfinic acid, a sulfinate salt, a alkyl sulfinate, or a sulfonamide.

In one general embodiment, the macrocyclic compound includes at least 4 naphthalene subunits, each having sulfonic acid-derived substituents at 3 and 6 ring-carbon positions, polar groups at 1 and 8 ring positions, and bridge linkages between the 2 ring-carbon position of one subunit and the 7 ring-carbon position of an adjacent subunit. One preferred compound of this type has the general structure:

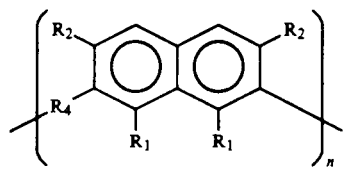

where $R_2$ is sulfonate salt, sulfinic acid, a sulfinate salt, an alkyl sulfinate, or a polar sulfonamide, such as $SO_2NHR$, where NHR is $NH_2$, NHOH, or an amino acid, $R_1$ is OH, =O, an alkyl or aryl ether, ester, or acid, or a mixture thereof, and n=4, 6, or 8, and $R_4$ is >CHR" or ≧CR", where R" is H or carboxylic acid group.

In another general embodiment, the macrocyclic compound includes at least 4 phenyl subunits with para-position sulfonic acid derived substitutents, bridge linkages between the 2 ring-carbon position of one subunit and the 6 ring-carbon position of an adjacent subunit. One preferred compound of this type has the general structure:

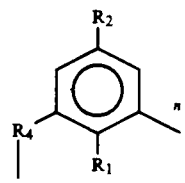

where n, $R_1$, $R_2$ and $R_4$ are as above.

For use in treating infection by an enveloped virus, the compound may be administered topically, e.g., in the treatment of herpes simplex infection. For treatment of systemic enveloped virus infection, the compound may be administered orally or parenterally. Such treatment method may further include administering to the subject a dose of protamine sulfate sufficient to reduce anti-coagulant effects of the compound.

In another aspect, the invention includes a method of inhibiting cell infection by an enveloped virus by administering to the site of infection a therapeutically effective dose of a biocompatible macrocyclic polymer having at least six regularly spaced sulfonic-acid derived substituents selected from the group consisting of an alkyl sulfone, and a sulfonamide of the form $SO_2NHR$, where NHR is $NH_2$, NHOH, or an amino acid.

In a preferred embodiment, the polymer is a macrocyclic compound composed or aryl ring subunits which are connected by ring-attached bridge linkages which form a continuous chain of connected atoms making up the backbone of the macrocycle, and which contain the sulfonic-acid derived substituents on non-backbone atoms of the aryl subunits.

Also forming part of the invention are novel compounds composed of aryl ring subunits which are connected by ring-attached bridge linkages which form a continuous chain of connected atoms making up the backbone of the macrocycle, and which contain, on non-backbone atoms of the aryl subunits, sulfonic-acid derived substituents selected from the group consisting of an alkyl sulfinate, and a sulfonamide of the form $SO_2NHR$, where NHR is $NH_2$, NHOH or an amino acid.

These and other objects and features of the invention will become more fully apparent when the following detailed description of the invention is read in conjunction with the accompanying drawings.

BRIEF DESCRIPTION OF THE DRAWINGS

FIG. 1 shows the general structure of a macrocyclic compound composed of naphthalene subunits, for use in the present invention;

FIGS. 2A and 2B show non-oxidized (2A) and partially oxidized (2B) forms of the FIG. 1 structure, where n=4 and the subunit is chromotropic acid;

FIGS. 3A and 3B illustrate two general methods of synthesis of a macrocyclic compound like the one shown in FIG. 2A;

FIGS. 14A and 14B are plots of HSV viral yields, as a function of drug dose, for the macrocyclic compounds KY-1 (14A) and KY-42 (14B);

DETAILED DESCRIPTION OF THE INVENTION

Definitions

Figure 4A:
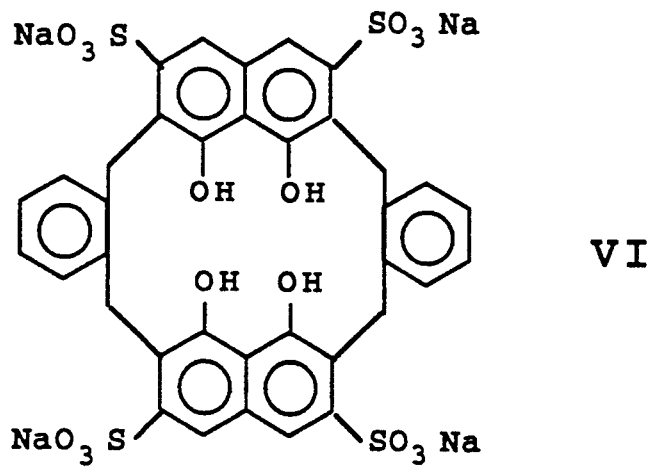
FIGS. 4A and 4B show an unoxidized (4A) and partially oxidized (4B) macrocycle with mixed phenyl and sulfonated naphthalene subunits.

The terms defined in this section have the following meanings unless otherwise indicated.

An "enveloped virus" means a virus containing a proteinaceous viral envelop which surrounds the viral capsid. Such enveloped viruses include orthomyxoviruses and paramyxovirus, herpes viruses, togaviruses and retroviruses. During cell infection by an enveloped virus, the plasma membrane of the host cell is altered to include some viral-coded proteins. As the viral nucleoprotein core exits the host cell, the core becomes enveloped enveloped with the modified membrane, thus forming the new viral envelop.

A "aryl ring" subunit is single ring or fused ring structure containing at least one aromatic ring, i.e., a 5-or 6-membered ring with the 6 pi electrons necessary for aromaticity. Examples include benzene, naphthalene, mixed aromatic and non-aromatic fused ring structures, such as tetralin, and heterocyclic structures, including fused-ring structures, such as quinoline, isoquinoline, and indole.

A "macrocyclic compound composed of aryl ring subunits" is a cyclic compound formed by linking ring atoms in aryl ring subunits to form a cyclic chain.

A "ring-attached bridge linkage" is a linkage between a ring atom of one aryl subunit to a ring atom of an adjacent aryl subunit in a macrocyclic compound;

The ring-attached bridge linkages and the (shorter path of) ring atom joining bridge linkages in the subunits collectively form a "continuous chain of connected backbone atoms". In the compound illustrated in FIG. 1, the chain is formed by the bridge linkages ($R_4$) to positions 2 and 7 of the naphthalene rings and the 5 ring atoms in naphthalene between positions 2 and 7. In the compound illustrated in FIG. 7, the chain is formed by the bridge linkages ($R_4$) to positions 2 and 6 of the benzene rings and the 3 ring atoms in benzene between positions 2 and 6.

Similarly, the "non-chain ring atoms" in the macrocycle are the ring atoms which are outside the bridge linkages. In the compound illustrated in FIG. 1, the non-chain atoms include the 5 naphthalene ring atoms from ring positions 3–6; in the FIG. 7 compound, the 3 ring atoms from positions 3–5.

A "sulfonic acid-derived substituent" includes sulfonic acid, a sulfonic acid salt, sulfinic acid, sulfinate salts, alkyl and aryl sulfinates, sulfonamides of the form $SO_2NHR$, where R is H or substituent having an OH, ether, ester, ketone, or acid moiety, and SH.

Preparing Aryl-Subunit Macrocyclic Compounds

This section describes the synthesis of two general types of aryl macrocyclic compounds which are useful in the anti-viral treatment method of the invention. The first type is composed of naphthalene subunits with sulfonic acid-derived substituents, described in subsection A. The second general type is composed of phenyl subunits having para-position sulfonic acid-derived substituents, described in subsection B. From the synthetic routes given in the two sections, it will be apparent how macrocycles composed of mixed subunits, e.g., both naphthalene and phenyl subunits can be prepared. The synthetic methods are also generally applicable to macrocycles composed of heterocyclic subunits with sulfonic acid-derived substituents.

Macrocyclic Compounds with Substituted Naphthalene Subunits

FIG. 1 shows the general structural formula of a macrocyclic compound composed of substituted naphthalene subunits, for use in the present invention. One exemplary compound of this type is shown in non-oxidized (I) and partially oxidized (II) form in FIGS. 2A and 2B, respectively. The compound is a tetramer of chromotropic acid (1,8-dihydroxy, 3,6-disulfonic acid naphthalene) subunits linked by methylene or methine ($>CH_2$ or $\geq CH$) bridges ($R_4$). As seen, the methylene bridges and the "interior" ring atoms (ring positions 1, 2, 7, and 8) form a continuous chain having $R_1$=OH or =O groups attached at the 1 and 8 positions. The non-chain atoms (ring positions 3–6 on each substituent) have $R_2$=sulfonic acid substituents on the 3 and 6 ring atoms. The nature of the partially oxidized structure was deduced from $H^1$ and $C^{13}$ NMR studies, and from mass spectroscopy evidence.

For purposes of the following discussion, and for illustrating synthetic routes, usually only the non-oxidized subunit form of the compound is given. It will be understood that the compound may be partially oxidized, after exposure to air under heat and acidic conditions, i.e., contain one or more $R_1$ ketone (=O) groups, and a double bond between the ring and the associated bridge methylene group, as indicated in FIG. 2B. It will also be understood that the same reaction mechanisms will apply generally to the partially oxidized form of the compound, i.e., the structure shown in FIG. 2B, or similar structures containing additional $R_1$ =O groups, except that $R_1$ modification reactions will typically selectively modify an $R_1$ —OH group, and leave the corresponding $R_1$ =O group intact.

As will be seen below, the compound preferably includes the chromotropic acid derivatives in which $R_1$ is a polar substituent, such as OH, =O, $CO_2H$ or an ether, thioether, ester, or thioester linked alkyl or aryl group, and combinations of these group, e.g., where only the OH groups in the partially oxidized structure are substituted by one of the above groups.

$R_2$, as noted, is a sulfonic acid-derived substituent which may be sulfonic acid, as shown in FIG. 2, a sulfonate salt, sulfinic acid (—$SO_2H$), and sulfinate salts, alkyl sulfinates, and sulfonamides. $R_3$ is H or Br or other halogen.

Also as will be seen below, the $R_4$ bridge linking the chromotropic acid derivative subunits is preferably of the form >CHR or ≧CR (indicating unsaturated bridges in the partially oxidized form), where R is H or a small carbon-containing group, such as lower alkyl, alkenyl, ketone, or carboxylic acid group, or aryl group. The bridge may also be of the form —$CH_2NR'CH_2$—, where R' is similarly H or a small carbon containing group, such as a lower alkyl group.

Alternatively, the bridges in the macrocycle may be ring structures, including aryl ring structures, such as in the dimeric macrocycle shown in FIG. 4, or analogous structures formed by bridging through heterocyclic rings, such as pyrole or furan rings.

The number of subunits may vary from 4 to 8, with macrocycles containing 4, 6, and 8 subunits being preferred. In the reaction schemes described below, the macrocycle formed may include mixtures of compounds with different subunit numbers (n) values, e.g., a dominant n=4 structure (4 subunits) with additional structures containing 6 and 8 subunits.

Representative macrocyclic compounds which have been synthesized and tested for anti-viral activity are identified by their $R_1$, $R_2$, $R_3$, and $R_4$ substituents in Table 1 below. The KY and Y number in the lefthand column in the table refers to the analog designation of the corresponding compound. For example, the compound in which $R_1$ is OH, $R_2$ is $SO_2NH_2$, $R_3$ is H, and $R_4$ is —$CH_2$— is designated KY-3. Although not shown in the table, the compounds may exist in a partially oxidized state in which one of more $R_1$ groups are =O, and adjacent bridges contain a double-bond carbon linkage to the ring.

TABLE 1

| KY | $R_1$ | $R_2$ | $R_3$ | $R_4$ |
|---|---|---|---|---|
| KY-1 | OH | $SO_3Na$ | H | >$CH_2$ |
| KY-3 | OH | $SO_2NH_2$ | H | >$CH_2$ |
| KY-42 | OH | $SO_3Na$ | H | >$CHCO_2H$ |
| KY-48 | OH | $SO_3Na$ | H | >$CHCHOHCH_2OH$ |
| KY-85 | OH | $SO_3Na$ | OH | >$CHC_6H_6$ |
| KY-97 | OH | $SO_3Na$ | H | >$CH_2CH=CH_2$ |
| KY-110 | OH | $SO_3Na$ | H | >$CHC(O)CH_3$ |
| KY-121 | OH | $SO_2C_6H_3(OH)_2$ | H | >$CH_2$ |
| KY-123 | OH | $SO_2Na$ | H | >$CH_2$ |
| KY-143 | OH | $SO_3Na$ | OH | >$CH_2$ |
| KY-147 | OH | $SO_2NHCH_3$ | H | >$CH_2$ |
| KY-148 | OH | $SO_2NHEt$ | H | >$CH_2$ |
| KY-151 | $OCH_3$ | $SO_3Na$ | H | >$CH_2$ |
| KY-158 | OH | $SO_2CH_3$ | H | >$CH_2$ |
| KY-171 | OH | SH | H | >$CH_2$ |
| KY-175 | OH | $SO_3CH_3$ | H | >$CH_2$ |
| KY-176 | OH | $SO_2NHC_6H_6$ | H | >$CH_2$ |
| KY-193 | OH | $SO_3Na$ | Br | >$CHBrCH_2Br$ |
| KY-194 | OH | $SO_3Na$ | Br | >$CH_2$ |
| KY-270 | $OCOCH_3$ | $SO_3Na$ | H | >$CH_2$ |
| KY-272 | $OCOCH_3$ | $SO_3Na$ | H | >$CHCO_2H$ |
| KY-276 | OCOEt | $SO_3Na$ | H | >$CH_2$ |
| KY-277 | COEtCl | $sO_3Na$ | H | >$CH_2$ |
| KY-280 | $OCH_3$ | $SO_3Na$ | H | >$CH_2$ |
| KY-281 | $OCOC_3H_7$ | $SO_3Na$ | H | >$CH_2$ |
| KY-284 | $OCH_3$ | $SO_3Na$ | H | >$CHCO_2H$ |
| KY-285 | $OCOCH_3$ | $SO_3Na$ | H | >$CH_2$ |
| KY-288 | OCOPr | $SO_3Na$ | H | >$CH_2$ |
| KY-289 | $OCOC_4H_9$ | $SO_3NH_4$ | H | >$CH_2$ |
| KY-290 | OCOBu | $SO_3Na$ | H | >$H_2$ |
| KY-291 | $OCOC_5H_{11}$ | $SO_3NH_4$ | H | >$CH_2$ |
| KY-293 | $OCOCH=CHCH_3$ | $SO_3NH_4$ | H | >$CH_2$ |
| KY-294 | $OCO(CH_2)_6CO_2H$ | $SO_3NH_4$ | H | >$CH_2$ |
| KY-307 | $O(CH_2)_5CO_2H$ | $SO_3NH_4$ | H | >$CH_2$ |
| KY-346 | OH | $SO_3Na$ | H | —$CH_2N(CH_3)CH_2$— |
| KY-352 | OH | $SO_3NHC_6H_{11}O_5$ | H | >$CH_2$ |
| KY-357 | OH | $SO_2NHCH_2CO_2Na$ | H | >$CH_2$ |
| KY-359 | OH | $SO_2NHOH$ | H | >$CH_2$ |
| KY-395 | $OCH_3$ | $SO_3Na$ | H | —$CH_2N(CH_3)CH_2$— |
| KY-397 | $OCH_3$ | $SO_2NH_2$ | H | >$CH_2$ |
| KY-398 | $OCH_3$ | $SO_2NHCH_2CO_2H$ | H | >$CH_2$ |

TABLE 1-continued

| KY | $R_1$ | $R_2$ | $R_3$ | $R_4$ |
|---|---|---|---|---|
| KY-399 | $OCH_3$ | $SO_2NHCH_2CO_2H$ | H | $-CH_2N(CH_3)CH_2-$ |
| Y-20 | OH | $SO_3Na$ | H | $-CH_2C_4H_2OCH_2-$ |
| Y-34 | OH | $SO_3Na$ | H | $-CH_2C_6H_4CH_2-$ |
| Y-66 | OH | $SO_3Na$ | H | $>CHCO_2H$ |
| KYY-19 | OH | $SO_2NHCH(CH_2)_2(CO_2H)_2$ | H | $>CH_2$ |

FIGS. 3A and 3B illustrate two preferred synthetic methods for preparing macrocyclic chromotropic acid compounds. The method illustrated in FIG. 3A involves cyclization of a chromotropic acid derivative (including chromotropic acid itself) with an aldehyde (RCHO) to form a macrocyclic compound, such as the tetramer shown FIG. 2, in which the chromotropic acid subunits are linked by R-substituted methylene groups, i.e., in which $R_4$ is $>CHR$ (including $\geq CR$). This synthetic scheme provides a convenient method for constructing macrocyclic compounds having a variety of different bridge-methylene R groups, by carrying out the cyclization reaction in the presence of an aldehyde of the form RCHO.

For example, to construct a macrocyclic compound with a $-CH_2-$ bridge, such as the KY-1 compound (IV), chromotropic acid (III) is reacted with formaldehyde. Typical reaction conditions are given in Example 1A for the synthesis of KY-1. Similarly, KY-42 is prepared by cyclization with glyoxylic acid (Example 1C); KY-48, in the presence of glyceraldehyde; KY-85, in the presence of benzaldehyde; KY-97, in the presence of acrolein; and KY-110, in the presence of pyruvic aldehyde. It will be appreciated that a variety of other RCHO aldehydes having small alkyl, alkenyl, acid and other hydrocarbon R groups would be suitable. Further, the R bridge group may be further modified after the cyclization reaction. For example, KY-193 may be prepared by bromination of the KY-97 compound.

In the method illustrated in FIG. 3B, cyclization of the chromotropic acid derivatives (III) is carried out by reaction with hexamethylenetetramine, to form a 3-atom chain bridge of the type $-CH_2N(CH_3)CH_2-$ (V). The cyclization reaction for the synthesis of KY-346 is given in Example 1J. The $-CH_2N(CH_3)CH_2-$ bridge may be modified, after the cyclization reaction, to form a variety of N-substituted bridges of the $-CH_2N(R')CH_2-$, where R' is one of a variety of small carbon-containing groups, according to known synthetic methods. Some of the bridges in the partially oxidized structure will have the form $=CHN(R')CH_2-$.

Figure 4B:
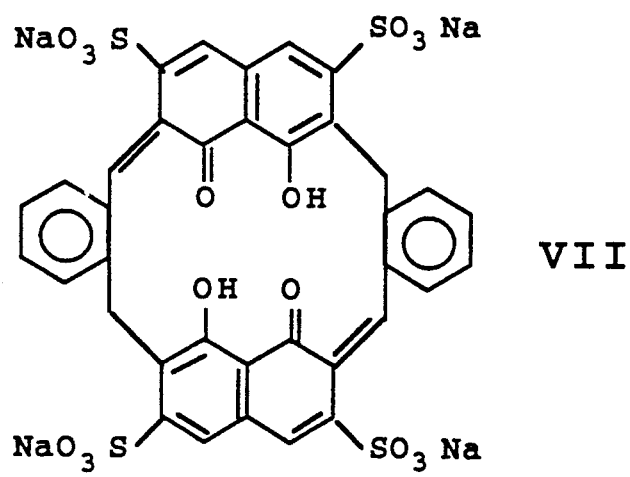

As noted above, the FIG. 4A compound (VI) is representative of macrocyclic naphthalene having a cyclic bridge, in this case a phenyl bridge. The compound is formed by reacting chromotropic acid, in the presence of hydrochloric acid with 1,2-benzenedimethanol in acetic acid, as detailed in Example 3. Similar methods can be employed to linked chromotropic acid subunits by other cyclic bridges, such as furan, pyrrole, thiophene, and the like. FIGS. 4A and 4B show the non-oxidized (VI) and partially oxidized (VIII) forms of the compound.

Figure 5:
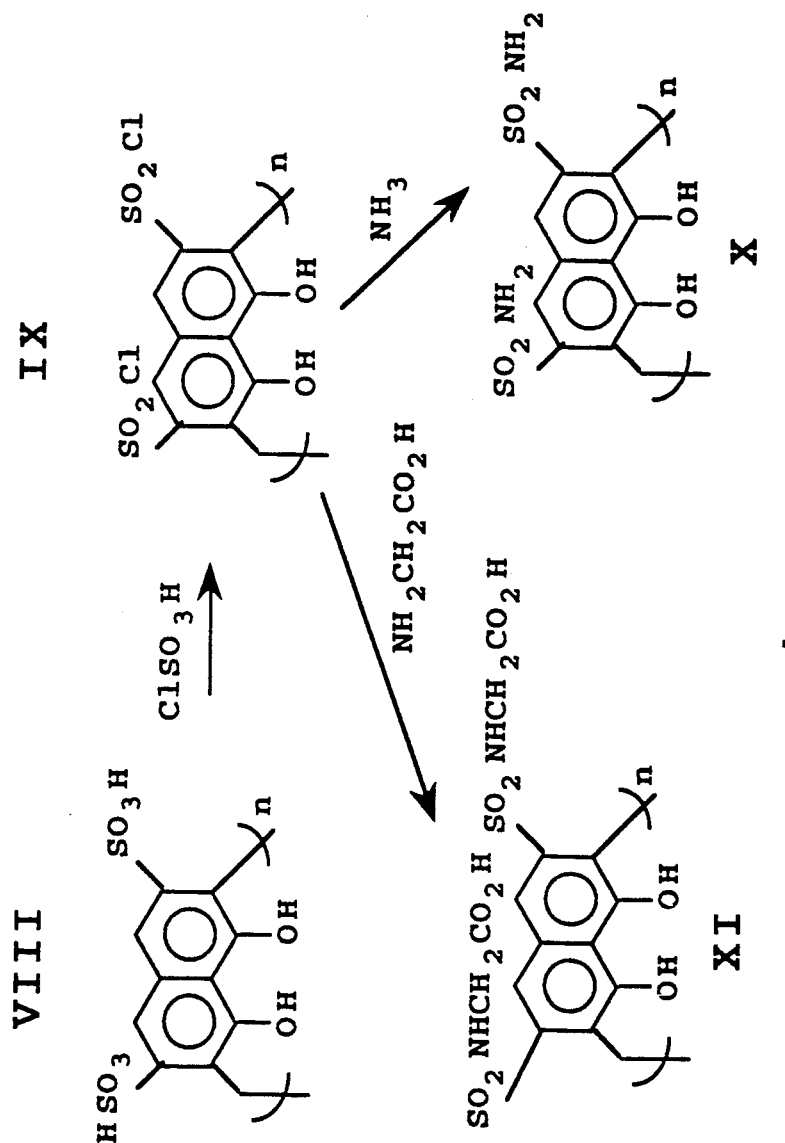
FIG. 5 illustrates reaction methods for converting the sulfonic acid substituents of macrocyclic chromotropic acid to glycyl sulfonamide and sulfonamide groups.

For synthesis of macrocyclic compounds with selected $R_1$, $R_2$, and $R_3$ substituents, two general approaches are available. In one approach, the chromotropic acid derivative is modified after cyclization so that the cyclized product will either contain the selected $R_1$, $R_2$, and $R_3$ substituent, or contain a substituent which can be readily modified to the selected substituent. This approach is illustrated by the synthesis of KY-3, which has an $SO_2NH_2$ $R_2$ substituent, as detailed in Example 1B. Here cyclized chromotropic acid (VIII) is reacted first with chlorosulfonic acid, to form the corresponding $R_2=SO_2Cl$ derivative (IX, FIG. 5). The macrocyclic compound is then reacted with ammonia water to form the desired $R_2=SO_2NH_2$ derivative (X, FIG. 5), as described in Example 1B.

A similar strategy was employed for the synthesis of KY-357 ($R_2=SO_2NHCH_2CO_2H$) by final subunit reaction with glycine (XI, FIG. 5), at basic pH.

Figure 6:
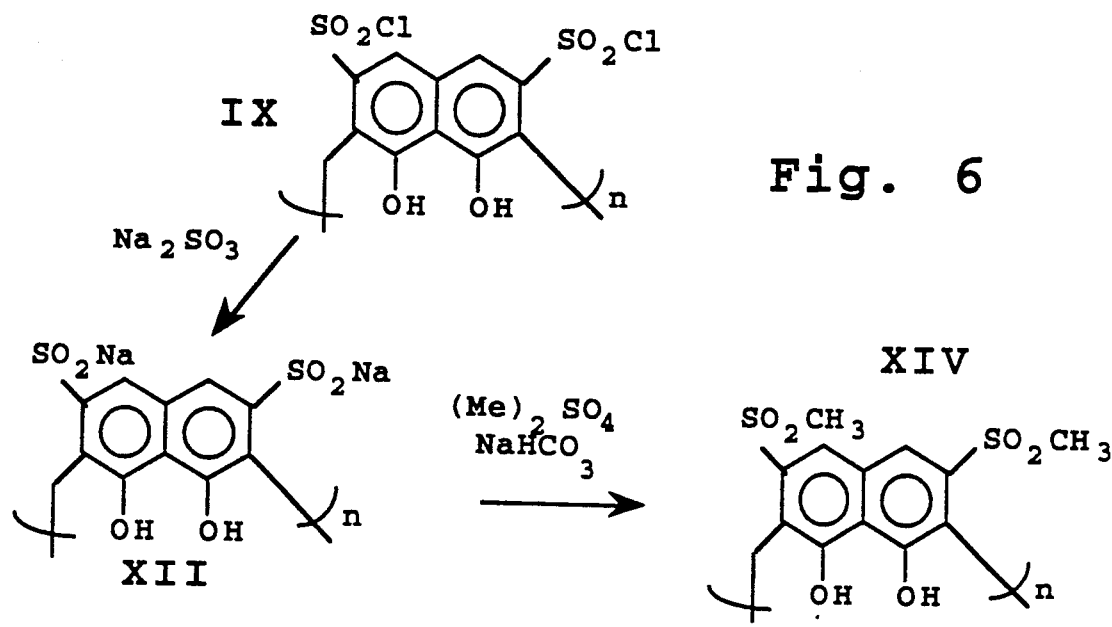
FIG. 6 illustrates a reaction method for converting the sulfonic acid residues of macrocyclic chromotropic acid to sulfinate salt or its methyl (aryl) ester.

FIG. 6 illustrates the conversion of sulfonyl groups of cyclized chromotropic acid to sulfinate salt (XII) and sulfinate methyl ester (XIV). The first stage of the reaction involves the formation of the corresponding sulfonyl chloride derivative (IX), as outlined above. This compound is then treated with sodium sulfite, to form the corresponding sulfinate salt (XII). Reaction with dimethyl sulfate in the presence of sodium bicarbonate produces the corresponding methyl sulfinate (XIV, KY-158, n=4).

Similarly, macrocyclic compounds with a variety of $R_1$ substituents may be prepared by modification of chromotropic acid after cyclization. In synthesizing KY-151, for example, ($R_1=OCH_3$) cyclized chromotropic acid is reacted with dimethylsulfate under basic conditions, as detailed in Example 1F, to form the methylether of cyclized chromotropic acid. Similarly, in preparing KY-307 ($R_1=O(CH_2)_5CO_2H$), cyclized chromotropic acid is first converted to the diether of hexanoic acid by initial reaction of cyclized chromotropic acid with 6-bromohexanoic acid under basic reaction conditions.

As further examples, in preparing compounds such as KY-272 and KY-294, in which $R_1$ has the form OCOR, the macrocyclic compound formed by cyclization of chromotropic acid is reacted with an acid chloride of the form RCOCl, under basic conditions, as detailed in Example 1I for the synthesis of KY-285.

In a second general approach, the selected substituent is formed on the subunit naphthalene rings by derivatization of the naphthalene subunit, with subsequent subunit cyclization to form the desired macrocycle. For the synthesis of KY-175 ($R_2=SO_3CH_3$), chromotropic acid is reacted with thionylchloride, as above, to produce the corresponding $R_2=SO_2Cl$ substituents. Further reaction with $NaOCH_3$ and cyclization leads to the desired $R_2$ substituent. Reaction details are given in Example 1H. Among other examples of this approach are KY-123 (Example 1G) and KY-147 (Example 1E).

It will be appreciated that the synthetic method for forming selected-substituent macrocyclic compounds may include both prior derivatization of chromotropic acid and subsequent derivatization of the subunits after cyclization. For example, in forming KY-397 ($R_1=OCH_3$, $R_2=SO_2NH_2$), chromotropic acid subunits are first reacted at the $R_1$ positions, to form the methyl ether derivative as described above. After cyclization with formaldehyde, the compound is further derivatized at the $R_2$ position, also as described above, to convert the SO₃Na group to the desired SO₂NH₂ substituent.

The KY compounds described above can be converted readily to a variety of sulfonic acid or sulfonate salts, by reaction in acid or in the presence of a suitable salt, according to well known methods. Thus, for example, several of the KY compounds shown in Table 1 are ammonium salts formed by cation exchange of protons in the presence of an ammonium salt, such as ammonium chloride. In addition, exposure of the macrocyclic compound to a variety of metal cations, such as the cations of Ca, Ba, Pt, Cu, Bi, Ge, Zn, La, Nd, Ni, Hf, or Pb, may produce both a metal salt and a metal chelate of the macrocyclic compound in which the metal is chelated at interior polar pocket in the compound.

The physical properties of several macrocyclic compounds prepared in accordance with the invention have been studied by absorption and mass spectrometry and by nuclear resonance spectroscopy (NMR), as detailed in Examples 1A, 1B, 1C, and 1J. These compounds include tetrameric macrocyclic compounds, such as indicated in FIG. 2, or mixtures with predominantly tetrameric forms.

Macrocyclic Compounds with Substituted Phenol Subunits

Figure 7:
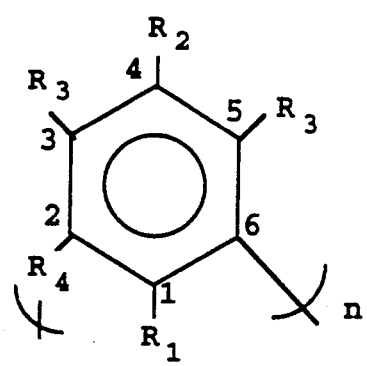
FIG. 7 shows the general structure of a macrocyclic compound composed of phenyl groups with para-position sulfonic acid-derived substitutents, for use in the present invention.
Figure 8:
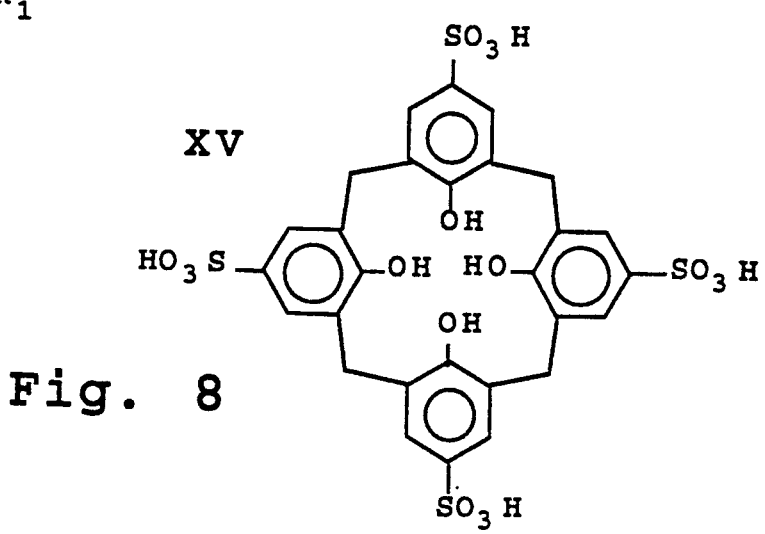
FIG. 8 shows a non-oxidized form of the FIG. 7 structure, where n=4 and the subunit is parasulfonic acid.

FIG. 7 shows the general structural formula of a macrocyclic compound composed of substituted phenol subunits, for use in the present invention. One exemplary compound of this type is shown in FIG. 8, which is a tetramer of phenol para-sulfonic acid subunits linked by methylene bridges (XV). As seen, the methylene bridges and the "interior" ring atoms (ring positions 2, 1, and 6) form a continuous chain having $R_1$=OH groups attached at the 1 ring positions. The non-chain atoms (ring positions 3-5 on each substituent) have $R_2$=sulfonic acid substituents on the 4 ring atoms.

Figure 9A:
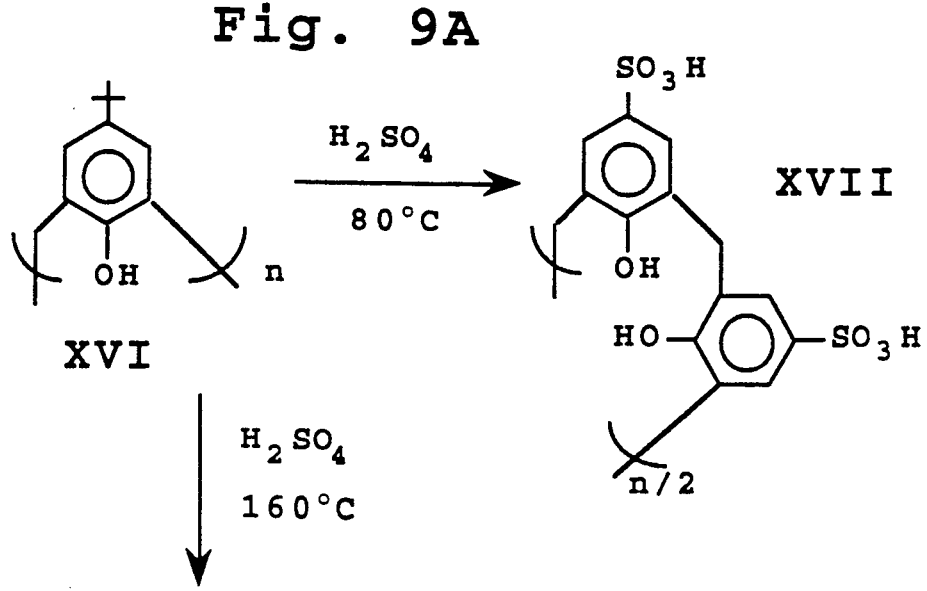
FIGS. 9A and 9B illustrate general methods of synthesis of non-oxidized and partially oxidized forms of the FIG. 8 compound.

FIG. 9A illustrates a general method for forming macrocyclic compounds of this type. The macrocyclic precursor shown at the left (XVI) is a class of compounds known generally as tert-butyl calix(n)arenes, where n is the number of phenolic subunits (with para-position t-butyl substituents) in the macrocycle, and the bridge connections are methylene groups. t-butyl calixarenes with 4, 6, and 8, subunits are commercially available.

In the sulfonation reaction shown in FIG. 9A, a t-butyl calixarene with a selected subunit number is treated with concentrated sulfuric acid, typically for about 4 to 5 hours at 75°-85° C. to effect substantially complete displacement of the 4-position t-butyl group by a sulfonic acid group. Details of the sulfonation reaction are given in Example 2A. The method has been used to produce the n=4 macrocycle compound shown in FIG. 8, and related macrocycles with 6 and 8 phenol subunits.

Figure 9B:
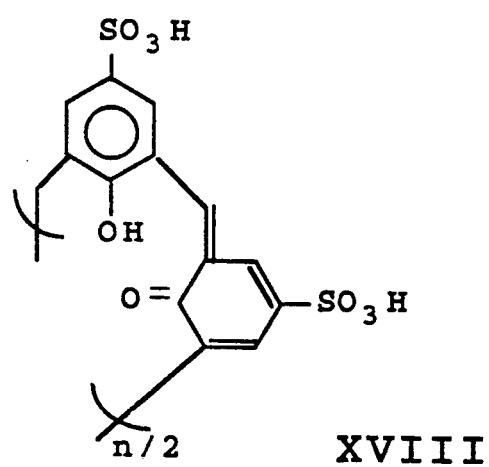

A similar method is used for preparing a sulfonated calixarene with partially oxidized 1-position OH groups, as shown at 9B. Here the t-butyl calixarene starting material is treated with conc. sulfuric acid at a temperature above 100° C., preferably between 150°-170° C. The reaction is effective to sulfonate the subunit rings and to partially oxidize the interior OH groups. As indicated in FIG. 9B, partial oxidation can lead to a conjugated macrocyclic structure (XVIII) in which bridge contributes delocalized electrons. This conjugated structure is colored, and the development of a colored product can be used to monitor the course of the oxidation reaction. Details of the reaction are given in Example 2B.

Figure 12:
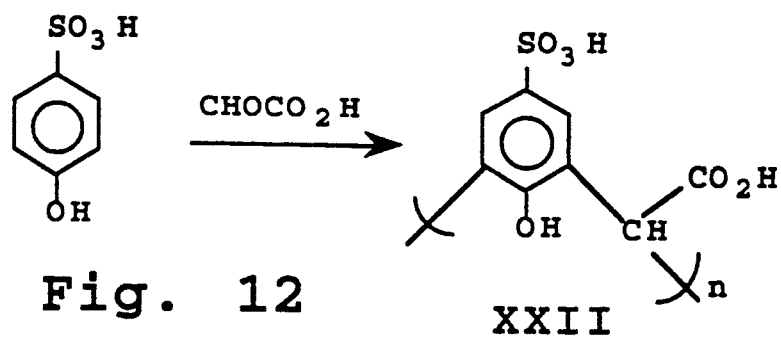
FIG. 12 shows a reaction scheme for producing a macrocylic compound like that shown in FIG. 8 but with carboxylic acid-containing bridge linkages.

It will be appreciated that the desired macrocycle can also be formed directly by reacting para-sulfonic acid phenol (or precursors thereof) under suitable bridging conditions, such as described above for producing naphthalene-subunit macrocycles. This is illustrated by the reaction shown in FIG. 12, for production of a macrocyle having carboxylic acid-containing bridge groups. In this method, phenol para-sulfonic acid is reacted with glyoxylic acid, under conditions similar to those described in Example 2C, to form the cyclized structure shown (XXII).

Figure 10:
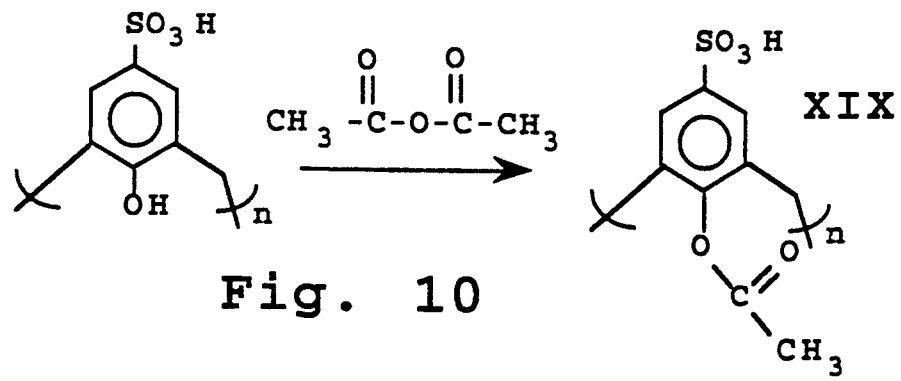
FIG. 10 shows a reaction scheme for replacing the ring hydroxyl groups in the FIG. 8 compound with acetyl groups.
Figure 11:
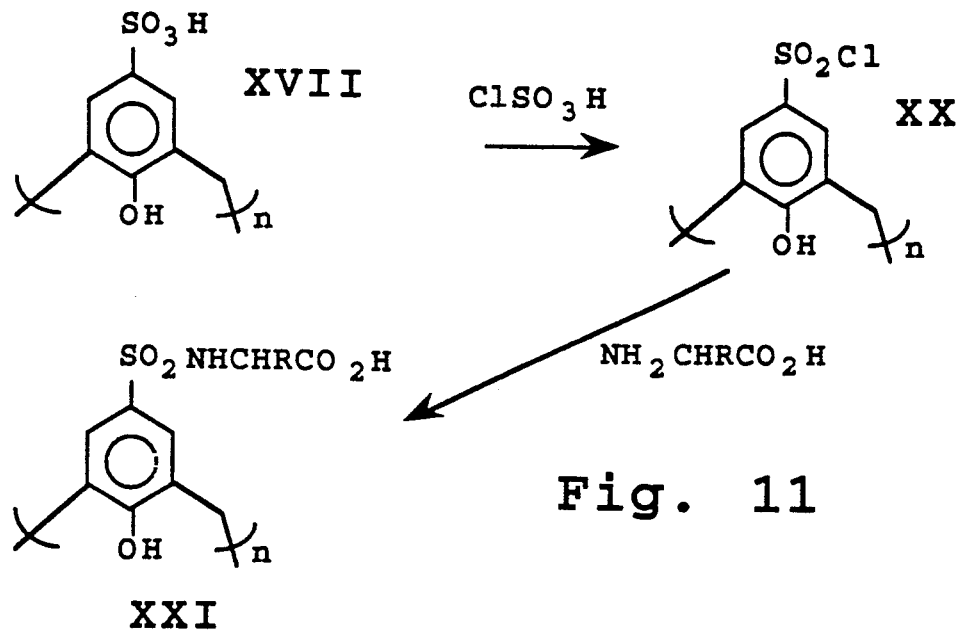
FIG. 11 shows a reaction for converting sulfonic acid substituents to a glycyl sulfonamide group in a phenyl-subunit macrocyclic compound.
Figure 13:
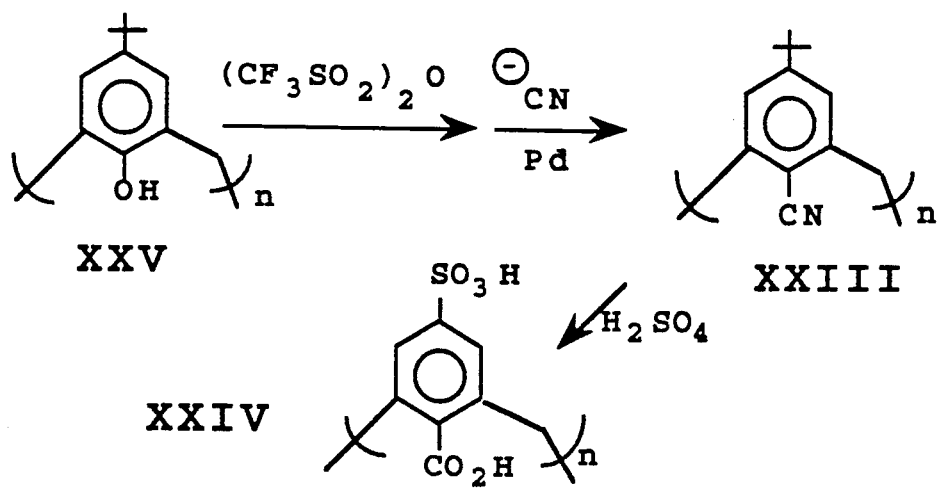
FIG. 13 shows a reaction scheme for replacing hydroxyl groups in the FIG. 8 compound with carboxylic acid groups.

The macrocyclic compounds formed as above can be modified, according to general procedures outlined in Section IIA above, to achieve selected $R_1$ groups, modified sulfonyl groups, and/or addition of $R_2$ groups. The range of $R_1$ and $R_2$ substitutents is substantially the same as that discussed above. FIGS. 10, 11, and 13 illustrate various reaction methods for modifying the $R_1$ group of an already formed macrocycle. In FIG. 10, the sulfonated structure shown in FIG. 8 is treated with acetic anhydride, to form an O-acetyl $R_1$ group. Details of the reaction are given in Example 2C. Since this structure would be expected to undergo hydrolysis in the presence of serum esterases, differences in the activity of the ester compound and the free OH compound would be expected to occur after intravenous (IV) administration. Example 2G describes a similar reaction scheme for forming a toluene sulfonic acid ester at the $R_1$ position.

FIG. 11 illustrates a general method for forming sulfonamides, such as glycylsulfonamide (XXI) of the FIG. 8 compound. Analogous to the reactions described with respect to FIG. 5, the sulfonated phenyl macrocyclic compound (XVII) is treated with chlorosulfonic acid, to form the corresponding sulfonyl chloride analog (XX). Further reaction with a selected amine, in this case glycine, gives the desired sulfonamide. Reaction details are given in Example 2D for the synthesis of the $R_2$=SO₂NH₂ compound and in Example 2E, for the synthesis of the glycyl sulfonamide compound.

FIG. 13 depicts a general synthetic method for a net substitution of $R_1$=OH by $R_1$=carbon moieties. In Example 2H, the reactions detail a process from which a substrate ($R_1$=OH, $R_2$=tert-butyl, $R_4$=CH₂, n=4) affords an intermediate ($R_1$=CN, $R_2$=tert-butyl, $R_4$=CH₂, n=4). Further modification then provides the product ($R_1$=CO₂H, $R_2$=SO₃H, $R_4$=CH₂, n=4).

It will be appreciated that substituent modifications at the $R_1$ site can be selectively carried out at OH sites in the partially oxidized macrocycle, such as the structure shown at FIG. 9B. That is, reactions which are specific for ring OH groups will leave the =O group intact, thus providing a mixed $R_1$ group containing =O groups.

The $R_4$ bridge linking the chromotropic acid derivative subunits is preferably of the form >CHR or ≧CR, where R is H or a small carbon-containing group, such as lower alkyl, alkenyl, ketone, or carboxylic acid group, or aryl group, as noted above, or of the form —CH₂NR'CH₂—, where R' is similarly H or a small carbon containing group, such as a lower alkyl group. Alternatively, the bridges in the macrocycle may be ring structures, including aryl ring structures, analogous to the dimeric macrocycle shown in FIG. 4.

Also as above, the number of subunits may vary from 4 (e.g., FIG. 4 structure) to 8, with macrocycles containing 4, 6 and 8 subunits being preferred. In the reaction schemes described below, the macrocycle formed may include mixtures of compounds with different subunit numbers (n) values, e.g., a dominant n=4 structure (4 subunits) plus additional structures containing 5-8 subunits.

Representative macrocyclic compounds which have been synthesized and tested for anti-viral activity are identified by their $R_1$, $R_2$, and $R_4$ substituents in Table 2 below. The KY and Y number in the lefthand column in the table refers to the analog designation of the corresponding compound, as in Table 1. Compounds which are partially oxidized at the $R_1$ position, and have which may have both saturated and unsaturated bridge methylene carbon groups are indicated as in Table 1.

TABLE 2

| Compound | $R_1$ | $R_2$ | $R_4$ | n |
|---|---|---|---|---|
| Y-1 | OH | $SO_3$ | —$CH_2$— | 8 |
| KY-226 | O/OH | $SO_3$ | —$CH_2$/=CH— | 8 |
| Y-49 | OH | $SO_3$ | —$CH_2$— | 4 |
| KY-225 | O/OH | $SO_3$ | —$CH_2$/=CH— | 4 |
| Y-77 | OH | $SO_3$ | —$CH_2$— | 6 |
| Y-48 | O/OH | $SO_3$ | —$CH_2$/=CH— | 6 |
| KY-268 | O/OH | $SO_3$ | —$CH_2$/=CH— | 3 |
| KY-269 | O/$CO_2CH_3$ | $SO_3$ | —$CH_2$/=CH— | 4 |
| KY-271 | O/$CO_2CH_3$ | $SO3$ | —$CH_2$/=CH— | 3 |
| Y-78 | O/OH | $SO_2NH_2$ | —$CH_2$— | 8 |
| Y-100 | O/OH | $SO_2OCH_3$ | —$CH_2$— | 8 |

The compounds shown in Table 2, and R-group combinations thereof, described above can be converted readily to a variety of sulfonic acid or sulfonate salts, by reaction in acid or in the presence of a suitable salt, according to well known methods, as described above.

Inhibition of Virus Infectivity

This section examines the ability of macrocyclic compounds of the invention to inhibit cell infection by a variety of enveloped viruses. The enveloped viruses which were examined are the herpes viruses, Herpes simplex virus-1 (HSV-1) and herpes simplex virus-2 (HSV-2), which are double-stranded DNA viruses (Roizman); human immuno-deficiency virus (HIV), an RNA retrovirus (Popovic; Barre-Simoussi); and influenza A and B and respiratory syncytial viruses (RSV), all RNA viruses (Chanock). For comparative purposes, selected non-enveloped viruses, including adenovirus, a double-stranded DNA virus (Rowe; Hilleman), and rhinovirus, a single-strand RNA virus (Dick), were examined. Typically, inhibition of virus infectivity was measured by the extent of inhibition of cytopathic effects detectable in infected cultured cells. Inhibition of HSV-1 and HSV-2 infectivity in cultured cells was also shown by inhibition of virus binding to infectable cells, and inhibition of viral plaque formation in infected cells, as described below.

In addition, a large number of representative aryl macrocyclic compounds (including those shown in Tables 1 and 2) were examined for toxicity in cell culture, using a panel of human cell lines, as detailed in Example 4. Briefly, the selected KY- or Y- compound was added to cell cultures at a final concentration of 5, 10, 25, 50, or 100 μg/ml. Three days later the cells were washed to remove drug, and stained with a vital stain, to determine the percentage of dead cells in each culture. The $IC_{50}$ drug concentration, i.e., value concentration of drug which produced 50% cell death, was 50 μg/ml for KY-143, KY-151, and KY-163, and 100 μg/ml or greater for all of the other KY compounds tested. For KY-1, which has a molecular weight of 1404 daltons, a drug concentration of 100 μg/ml is equivalent to about 66 μM.

Inhibition of HSV Infectivity: Naphthalene-Subunit Compounds

Several of the compounds in Tables 1 and 2 were tested for inhibition of cytopathic effects (CPE's) in cultured, HSV-infected cells. In the method reported in Example 5, Vero cells were infected with HSV-1 or HSV-2 and allowed to grow in culture until cytopathic effects were clearly visible. In the absence of infection, the cells form an even monolayer of fibroblast-like cells. With HSV infection, a cytopathic effect characterized by round cells in suspension is clearly evident after 24 hours, followed by clumping and lysis of infected cells after 24-72 hours.

In the drug inhibition study reported in Example 5, cells were exposed to HSV-1 or HSV-2 virus and, at the same time, to a selected aryl macrocyclic drug, at a final drug concentration of 10 μg/ml. Twenty-four hours later the cells were examined for cytopathic effect. If a clear cytopathic effect was not observed with 10 μg/ml of the drug, the study was repeated at a drug concentration of 20 μg/ml for some compounds.

Table 3 below lists 50 naphthalene-subunit macrocycles which were tested in this assay. A "+" symbol in the second column indicates that the compound was effective in inhibiting cytopathic effects at 10 or 20 μg/ml. A "—" symbol indicates that CPE was observed at 10 or 20 μg/ml.

TABLE 3

| Compound | CPE 10, 20 μg/ml | HSV-1 $IC_{50}$ (μg/ml) | HSV-2 $IC_{50}$ (μg/ml) |
|---|---|---|---|
| KY-1 | + | 2.7 | 1.7 |
| KY-3 | + | 2.4 | 2.5 |
| KY-42 | + | 1 | 3 |
| KY-48 | — | $N^1$ | N |
| KY-85 | — | N | N |
| KY-97 | + | N | N |
| KY-110 | — | N | N |
| KY-121 | + | 1.5 | 1.8 |
| KY-123 | + | 1.5 | 1.5 |
| KY-129 | + | 1 | 1 |
| KY-143 | — | N | N |
| KY-147 | — | N | N |
| KY-148 | — | N | N |
| KY-151 | + | 1.25 | 1.8 |
| KY-158 | — | N | N |
| KY-171 | + | 2.5 | 3 |
| KY-175 | — | N | N |
| KY0176 | N | N | N |
| KY-193 | GC | N | N |
| KY-194 | + | 1 | 1 |
| KY-280 | + | 2 | 2 |
| KY-272 | + | N | N |
| KY-276 | + | 1.3 | 1.2 |
| KY-277 | + | 1 | 1.2 |
| KY-280 | + | 1.1 | 1 |
| KY-281 | + | 0.5 | 1.5 |
| KY-284 | + | 1 | 1.6 |
| KY-285 | + | 1 | 1.5 |
| KY-286 | + | 2 | 2 |
| KY-288 | + | 1.7 | 2 |
| KY-289 | + | 2.2 | 1.7 |
| KY-290 | + | 1.2 | 1.3 |
| KY-291 | + | 1.4 | 2 |
| KY-293 | + | 1.9 | 2.7 |
| KY-294 | + | 1 | 2.2 |
| KY-301 | + | 1 | 1 |
| KY-307 | + | .8 | 2 |
| KY-308 | + | .9 | 1.2 |
| KY-345 | + | 5 | 6.7 |
| KY-346 | + | 4.4 | 6.2 |

TABLE 3-continued

| Compound | CPE 10, 20 µg/ml | HSV-1 IC$_{50}$ (µg/ml) | HSV-2 IC$_{50}$ (µg/ml) |
|---|---|---|---|
| KY-352 | + | 3.4 | 4.1 |
| KY-357 | + | 4 | 3.3 |
| KY-359 | + | 5.75 | 4.2 |
| KY-376 | + | 2.7 | 1 |
| KY-395 | − | N | 9 |
| Y-4 | + | 5.5 | 6.4 |
| Y-14 | + | 2.5 | 3.5 |
| Y-20 | + | 5 | 3.2 |
| Y-34 | + | 2.5 | 2 |
| Y-66 | + | N | N |

[1]N, no inhibition of CPE observed at highest concentration tested, or insufficient inhibition observed to predict IC$_{50}$.

The compounds used in Table 3 were further tested for activity against HSV infection in a plaque reduction assay, as detailed in Example 6. Here Vero cells, after overnight incubation, were exposed to serial dilutions of KY compound, from 0.625–10 µg/ml, and HSV-1 or HSV-2 virus for two hours. After washing to remove drug and extracellular virus, the cells were further incubated for 2 days, then stained and counted for plaque formation. Percent inhibition was determined by dividing plaques produced by total number of plaques in infected, untreated controls. From the concentration effect curve of plaque inhibition (expressed as percent of control), the concentration of compound required to produce 50% plaque reduction, IC$_{50}$, was determined. The IC$_{50}$ values for infection by HSV-1 and HSV-2 infection is given in the right-hand columns in Table 3.

With reference to the compound structures given in Table 1, the following Regroup features can be identified as contributing to low activity (no protection of cells from CPE effect seen at 10–20 µg/ml: in KY-48, KY-49 and KY-110, a bulky side chain in the methylene bridge; in KY-143, an OH R$_3$ group; in KY-147 and KY-148, a sulfonamide with a non-polar alkyl group at the R$_2$ position; in KY-158 and KY-175, a sulfone or sulfonyl with a non-polar alkyl group at the R$_2$ position; and in KY-395, a trimethylamine bridge in combination with a methyl ether substituent at the R$_1$ position. The "GC" symbol for KY-193 means that some giant cells were formed, indicating partial inhibitory activity.

Despite the lower activity of alkyl sulfinate compounds, these compounds have the in-vivo potential for conversion to the corresponding acid compound by esterase action.

Looking now at the compounds which give complete CPE at 10–20 µg/ml, the following Regroup structures can be identified as preferred radicals:

The R$_1$ position contains OH, including combinations of OH and =O groups; alkyl and aryl esters, including combination of such esters and =O; and alkyl ethers, including combinations of such ethers and =O.

The optimal radicals at the R$_2$ position are sulfonic acid or sulfonic acid salts, sulfinic acid and salts thereof, and sulfonamides with polar amine groups, such as NH$_2$, NHOH, N-glycosides (KY-352), and amino acids.

The preferred radicals at the R$_3$ position are H or Br.

The optimal bridge linkage groups are substituted and unsubstituted methylenes, where the R group is not a bulky alkyl group, and preferably a carboxylic acid group.

As a further guide to R-group selection, compounds having an ED$_{50}$ value of ≦1 µg/ml for at least one of the two HSV tests have one of the following R-group characteristics:

Compounds whose R$_1$ groups are lower-alkyl ethers or esters, or contain a terminal carboxylic acid group are typically most active, especially in combination with =O groups at other R$_1$ sites in the compound.

The R$_2$ groups are sulfonic acid or sulfonic acid salts or sulfonamides with a terminal carboxylic acid. This feature indicates that an R$_2$ position acid group favors high activity.

The R$_4$ bridge is methylene or a methylene carrying a carboxylic acid (acetyl) group.

The ability of selected naphthalene-subunit compounds to inhibit HSV-1 and HSV-2 viral yields at selected drug concentrations up to 10 µg/ml was assessed in the viral inhibition assay described in Example 7. Briefly, cultured Hela cells were exposed to serially diluted KY compound and virus, allowed to grow for 24 hours, then freeze/thawed 3 times to release virus particles. Vero cells infected with serial dilutions of the viral lysates were assayed for plaque counts as described in Example 6. The drop in viral yield, as a function of drug concentration, is plotted in FIGS. 14A and 14B for compounds KY-1 and KY-42 respectively. The dose dependent drop in viral yield was between about 3–5 orders of magnitude, depending on drug and virus. The degree of inhibition of viral yield was generally greater for HSV-1 than for HSV-2. Similar results were observed with several other KY compounds.

Inhibition of HSV Activity: Phenyl Subunit Compounds

A similar study of anti-HSV activities was carried out with several of the phenyl macrocyclic compounds listed in Table 2 above, with the results shown in Table 4. As seen from column 2 of the table, all of the compounds which were tested gave inhibition of CPE at 10–20 µg/ml. Inhibition activity of the tested compounds against HSV-I and HSV-2 in the plaque reduction assay is shown in the two righthand columns in the table (given as IC$_{50}$ in µg/ml)

TABLE 4

| Compound | CPE 10, 20 µg/ml | HSV-1 IC$_{50}$ (µg/ml) | HSV-2 IC$_{50}$ (µg/ml) |
|---|---|---|---|
| Y-1 | + | 7 | 7.2 |
| KY-226 | + | 1.6 | 3 |
| Y-49 | + | 5 | 10 |
| KY-225 | + | 1.8 | 1.8 |
| Y-77 | + | 8 | 11 |
| Y-48 | + | 1.5 | 1 |
| KY-268 | + | 4.4 | 1.5 |
| KY-269 | + | 2.4 | 2.3 |
| KY-271 | + | 4.2 | 2.4 |

The highest activities observed for the phenyl-subunit compounds are comparable to the highest activities seen with the naphthyl compounds, e.g., from about 1–3 µg/ml IC$_{50}$ values.

The most active compounds, Y-226 (n=8), Y-48 (n=6), and Y-225 (n=4) all have partially oxidized R$_1$ OH/=O groups, and each partially oxidized compound is substantially more active than its corresponding non-oxidized analog.

The partially oxidized n=3 compound, KY-268, is somewhat less active than its n=4, 6, and 8 analogs. Among the non-oxidized compounds, the n=8 compound, Y-1, is somewhat more active than the corresponding n=4 and n=6 compounds.

Addition of acetyl groups at the $R_1$ position produces little change in the activities of partially oxidized compounds, also consistent with the results observed with the naphthalene-subunit compounds, addition of alkyl esters at the $R_1$ positions gave activities comparable to the partially oxidized analog.

As a general guide to optimizing compound activity in the phenyl-subunit compounds, the same rules discussed above generally apply. Thus, for example, highest activity is expected when the $R_2$ group is a sulfonic acid, or a sulfinate ester or sulfonamide with a polar or acid R group. Similarly, highest activity is expected when the $R_1$ group is an ether, ester, acid group, preferably in combination with =O $_1$ groups.

Comparison of Anti-HSV Compounds

The inhibitory effect of KY-1 against drug-resistant strains of HSV-1 and HSV-2 was compared with several anti-viral agents which have been used in treating HSV infection. These compounds tested were the nucleoside analogs acyclovir (ACV), ganciclovir (DHPG), phosphonoformate (PFA), and phosphomethoxyethyladenine (PMEA). Inhibition of viral yield was determined, as above, by infecting Hela cells in the presence of wild type or drug-resistant strains of HSV-1 or HSV-2, and serial dilutions of a selected anti-viral compound, and infecting Vero cells with serial dilutions of the Hela cell lysate, as above. Details of the inhibition study are given in Example 8.

The $ID_{90}$ concentration (which effects 90% inhibition of viral yield) is given in Table 5. The KOS (HSV-1) and 333 (HSV-2) are wild type viruses; the KOS (PMEA)' and KOS (PFA)' are drug-resistant HSV-1 strains having a DNA polymerase mutation. The 333(DHPG) strain is a drug-resistant HSV-2 strain having a thymidine kinase mutation. With the exception of DHPG as an inhibitor of drug-resistant strains of HSV-1, and PMEA as an inhibitor of drug-resistant strains of HSV-2, all of the nucleoside analogs were at least about 20 times less active against drug-resistant strains than wildtype strains of either HSV-1 or HSV-2, as measured by drug concentration required to inhibit yield. By contrast, the aryl macrocyclic compound showed substantially the same specific activity against drug-resistant strains of HSV-1 and HSV-2 as against wild-type strains.

Inhibition of RSV and Influenza A Virus Infectivity

Representative macrocyclic compounds from Table 1 were tested for inhibition of cytopathic effects in cultured MDCK or HEp2 cells after infection by Influenza A virus (A/Taiwan strain) or RSV virus. In the method of inhibiting virus infectivity by influenza A, MDCK cells were infected with the virus, and the cells were allowed to grow in culture until cytopathic effects were clearly visible. In the absence of infection, the cells form an even monolayer of fibroblast-like cells. With virus infection, a cytopathic effect characterized by cell clumping is observed. For each compound tested, drug concentrations of 0.1, 1, 10, 25, and 100 μg/ml were added to cultured cells at the time of virus infection, as detailed in Examples 9 and 11. Twenty-four hours later the cells were examined for percent clumping, based on the percent of clumped cells of total cell particles in a given view field. The inhibition of clumping was plotted as a function of drug concentration, to determine the dose effective to produce a 50% reduction in the percent clumped cells, measured with respect to control (no drug treatment). The measured $ED_{50}$ values are given in Table 6 below.

A similar method was employed to determine the $ED_{50}$ of RSV inhibition of cytopathic effect (cell clumping) in HEp2 cells, with the results shown in Table 6. Details are given in Example 9.

TABLE 6

| | $ED_{50}$ (μg/ml) | |
|---|---|---|
| Compound | Influenza A (Taiwan) | RSV |
| KY-1 | >188 | 0.19 |
| KY-3 | 6 | 0.75 |
| KY-42 | 94 | 1.50 |
| KY-47 | 94 | >250 |
| KY-85 | >250 | 1 |
| KY-97 | 5 | 0.5 |
| KY-110 | >250 | 4 |
| KY-123 | 31.3 | 1 |
| KY-151 | >94 | 1.5 |
| KY-193 | 5.0 | 0.8 |
| KY-194 | 7.9 | 0.5 |

In general, RSV was significantly more sensitive to compound inhibition than the Influenza A/Taiwan virus. Highest-IAV activity was seen with a sulfonamide with polar amine ($SO_2NH_2$) at the $R_2$ position, and with selected methylene bridge groups. Relatively high anti-

TABLE 5

| | Strain/ | | Drug Tested ($ID_{90}$) # | | | | |
|---|---|---|---|---|---|---|---|
| Virus | drug selection | Mutation Locus | KY-1 (ug/ml) | ACV (uM) | DHPG (uM) | PFA (uM) | PMEA (uM) |
| HSV-1 | KOS | None | 1.9 | 14 | 2 | 180 | 100 |
| | KOS (PMEA)' | DNA pol | 2.6 | 380 | NT | 3000 | >2000 |
| | KOS (PFA)' | DNA pol | 4.3 | 100 | 1 | >1000 | >1000 |
| HSV-2 | 333 | None | 3.2 | ≈10 | 2 | 150 | 155 |
| | 333 (DHPG)' | TK | 3.7 | >100 | 215 | NT | 120 |

The data demonstrate that aryl macrocyclic compounds are effective against drug-resistant HSV strains at drug concentrations comparable to those which are effective against wild type virus strains. By contrast, and with the exception of DHPG as an inhibitor of HSV-1 strains, both drug-resistant strains showed a significant resistance to ACV, DHPG, PFA, and PMEA, as evidenced by the severalfold greater $ID_{90}$ drug concentrations required for virus inhibition.

RSV activity was seen with all compounds except KY-47.

Inhibition of HIV Infectivity: Naphthalene-Subunit Compounds

Representative macrocyclic compounds from Table 1 were tested for inhibition of cytopathic effects in cells infected with one of two HTLV-III strains, HTLV-III$_B$ and RF-II strains, as described in Example 12.

Briefly, cells chronically infected with HTLV-III$_B$ or RF-II HIV strains were incubated in the presence of serial dilutions of the selected KY compound, then further cocultured with indicator cells. The extent of syncytia formation was scored under phase microscopy. The concentration (μg/ml) effective to produce complete inhibition of syncytia formation, ED$_{100}$, is shown in Table 7 for the two HIV strains. The "N" means that the compound was not tested for that virus.

TABLE 7

Inhibition of Syncytia Formation

| Compound | HIV-HXB ED$_{100}$ | HIV-RF-II ED$_{100}$ |
|---|---|---|
| KY-1 | 8 | N |
| KY-3 | 16 | N |
| KY-42 | 8 | N |
| KY-48 | 250 | N |
| KY-85 | 32 | N |
| KY-97 | 32 | N |
| KY-110 | 63 | N |
| KY-121 | 16 | 16 |
| KY-123 | 16 | 16 |
| KY-129 | 16 | 8 |
| KY-143 | 250 | 125 |
| KY-147 | 250 | 250 |
| KY-148 | 250 | N |
| KY-151 | 32 | 125 |
| KY-158 | 500 | 7500 |
| KY-171 | 125 | 250 |
| KY-175 | 63 | 250 |
| KY-176 | 125 | 250 |
| KY-193 | 63 | 500 |
| KY-194 | 63 | 125 |
| KY-270 | 16 | 32 |
| KY-272 | 63 | 250 |
| KY-276 | 16 | 32 |
| KY-277 | 16 | 32 |
| KY-280 | 16 | 32 |
| KY-281 | 16 | 32 |
| KY-284 | 16 | 32 |
| KY-285 | 16 | 32 |
| KY-286 | 16 | 32 |
| KY-288 | 8 | 16 |
| KY-289 | 16 | 32 |
| KY-290 | 16 | 32 |
| KY-291 | 16 | 32 |
| KY-293 | 16 | 63 |
| KY-294 | 16 | 16 |
| KY-301 | 8 | 8 |
| KY-307 | 8 | 32 |
| KY-308 | 8 | 32 |
| KY-345 | 63 | 125 |
| KY-346 | 16 | 32 |
| KY-352 | 32 | 125 |
| KY-357 | 32 | 63 |
| KY-359 | 32 | 63 |
| KY-376 | 8 | 16 |
| KY-395 | | |
| Y-4 | 8 | 125 |
| Y-14 | 16 | 32 |
| Y-20 | 4 | 16 |
| Y-34 | N | N |
| Y-66 | N | N |

As seen from these results there is a general correlation between anti-viral activity against the two strains; that is, compounds which are most active against the HTLV-III$_B$ strains are also most active against the RF-11 strain.

With reference to the compound structures given in Table 1, the following R-group features can be identified as contributing to sub-optimal activity (ED$_{100}$ values $\geq 63$ μg/ml for both strains): in KY-48, a bulky side chain in the methylene bridge; in KY-110, a methyl ketone group in the bridge; in KY-143, an OH R$_3$ group; in KY-147 and KY-148, a sulfonamide with a non-polar alkyl group at the R$_2$ position; in KY-158 and KY-175, a sulfinate ester or sulfonate ester with a non-polar alkyl group at the R$_2$ position; and in KY-272, a methyl ester at the R$_1$ position combined with an acetyl-group bridge. These features are substantially the same as those which gave reduced activity against HSV viral infectivity, i.e., showed no inhibitory effect on CPE at 10–20 μg/ml.

Similarly, those factors which promote high activity against HSV activity are in general the same as those which give highest activity against HIV infectivity. These factors include: the groups at the R$_1$ position are OH, including combinations of OH and =O groups; alkyl and aryl esters, including combination of such esters and =O; and alkyl ethers, including combinations of such ethers and =O.

The preferred radicals at the R$_2$ position are sulfonic acid or sulfonic acid salts, sulfinic acid and salts thereof, and sulfonamides with polar amine groups, such as NH$_2$, NHOH, N-glycosides (KY-352), and amino acids, with sulfonic acid. In particular, high activity was seen with sulfonic acid, sulfonate salts, and sulfonamides having a terminal carboxylic acid group.

The optimal radicals at the R$_3$ position is H, with both OH and Br giving reduced activity.

The bridge groups are preferably substituted and unsubstituted methylenes, where the R group is not a bulky alkyl group.

As a further guide to R-group selection, compounds having an ED$_{50}$ value of $\leq 1$ μ/ml for at least one of the two HSV tests have one of the following R-group characteristics:

Compounds whose R$_1$ groups are lower-alkyl ethers or esters, or contain a terminal carboxylic acid group are typically most active, especially in combination with =O groups at other R$_1$ sites in the compound.

The R$_2$ groups are sulfonic acid or sulfonic acid salts or sulfonamides with a terminal carboxylic acid. This feature indicates that an R$_2$ position acid group favors high activity.

The R$_4$ bridge is methylene or a methylene carrying a carboxylic acid group.

These preferred R-groups are intended to provide guidance in the selection of R groups at the R$_1$–R$_4$ positions, for optimizing compound efficiency.

Inhibition of HIV Infectivity: Phenyl-Subunit Compounds

Representative macrocyclic compounds from Table 2 were tested for inhibition of cytopathic effects in cells infected with one of two HTLV-III strains, HTLV-III$_B$ and RF-II strains, as described in Example 12, and in the subsection above. The IC$_{50}$ values measured for the HXB and RS-11 strains of HIV are given in units of μg/ml in Table 8 below.

TABLE 8

| Compound | HIV-HXB IC$_{50}$ | HIV-RF-11 IC$_{50}$ |
|---|---|---|
| Y-1 | 16 | N |
| KY-226 | 16 | 250 |
| Y-49 | N | N |
| KY-225 | 32 | 125 |
| Y-77 | N | N |
| Y-48 | N | N |
| KY-268 | 32 | 32 |
| KY-269 | 32 | 32 |
| KY-271 | 32 | 63 |

Interestingly, the Y-1 compound and KY-226 (the corresponding partially oxidized analog) have comparable activities against the HXB strain, in contrast to the significantly higher activity of KY-226 seen against HSV viruses. All of the other compounds tested have partially oxidized $R_1 =\!\!=\!\! O$ groups, and all compounds give comparable activity.

Specificity Toward Enveloped Viruses

This section examines the specificity of the viral-inhibition inhibition method to enveloped viruses. The studies reported in subsection A show that the macrocyclic compounds used in the method act, at least in part, by binding selectively to viral envelop proteins, and that this binding blocks virus attachment to infectable cells, thereby inhibiting virus infectivity. These studies are detailed in parent U.S. patent application Ser. No. 647,720, filed Jan. 29, 1991. Subsection B examines the inhibitory effect of the macrocyclic on non-enveloped viruses.

Mechanism of Viral-Infection Inhibition

Figure 15:
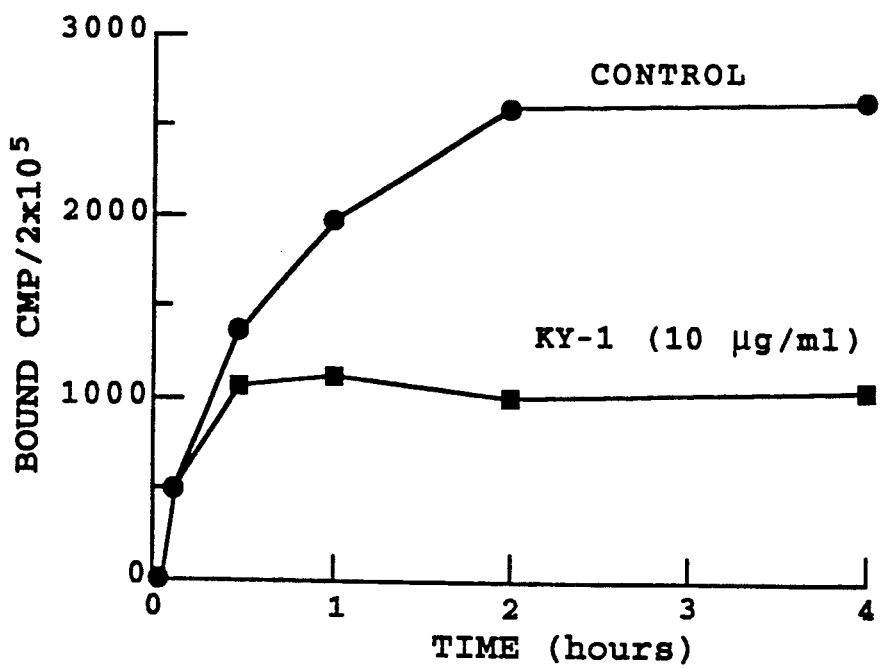
FIG. 15 shows the inhibition of $^3$H-labeled HSV-1 binding to cells by the compound KY-1.

In one study, the ability of a macrocyclic compound to block HSV binding to infectable cells was examined as described in Example 14. Briefly, Vero cells were exposed to radiolabeled HSV-1 or HSV-2 in the absence of KY compound or in the presence of 10 µg/ml KY-1, and binding of the virus at times up to 4 hours after exposure to the virus was measured. FIG. 15 shows a plot of virus (radiolabel) binding to cells over the four-hour incubation period. In the absence of drug, the amount of bound virus increased steadily over two hours, and slightly from 2-4 hours. By contrast, virus binding to cells peaked at about ½ hour in the presence of drug, presumably reflecting the time during which the binding events effective to block virus binding to the cells are equilibrating.

Figure 16:
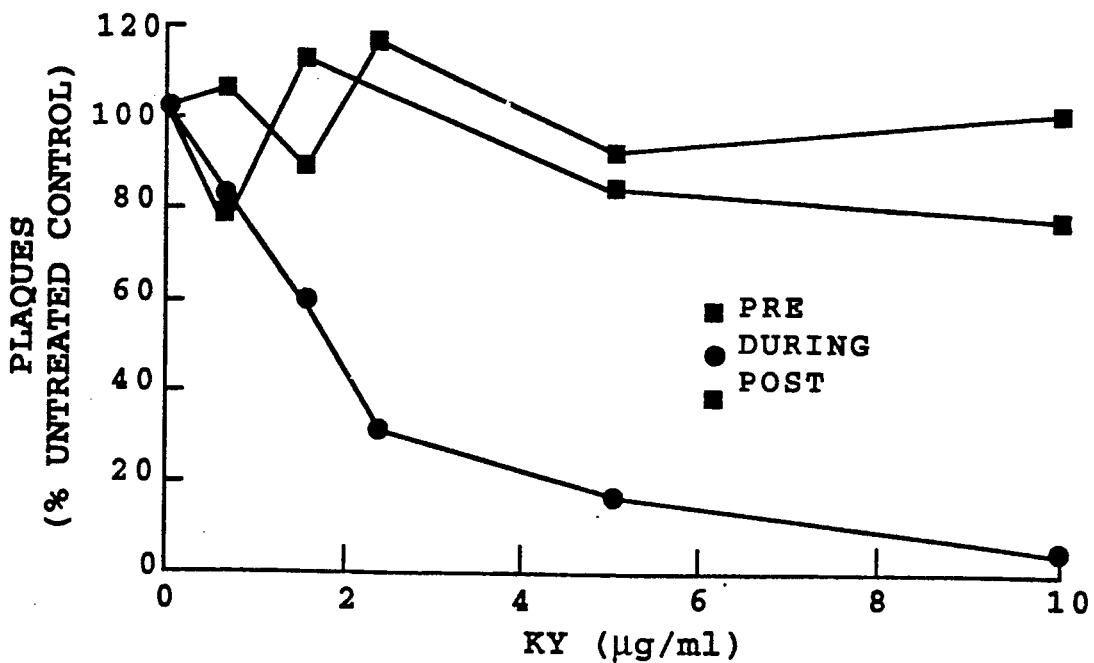
FIG. 16 is a plot of the inhibition in plaque formation of HSV-1 virus when the virus is exposed to the compound KY-1 before (open squares), (ii) after (closed squares), and during (closed circles) incubation with Vero cells.

In a second study, the effect of compound when administered prior to, during, or after cell infection by HSV-1 was examined as described in Example 15. In these studies, cells were exposed to one of a series of increasing KY-2 concentrations, and the extent of infection was measured by number of plaques observed 24 hours after infection. The reduction in plaque formation, expressed as a percent of control, is shown in FIG. 16 for cells treated with drug prior to (solid rectangles), during (closed circles), and after (open rectangles). Virus inhibition was seen most significantly when the cells were treated with drug during exposure to virus, indicating that virus inhibition occurs at the period of virus binding to and entry into infectable cells.

In a third study, purified HSV-1 virus suspensions were incubated with KY-1 or the sodium salt thereof, or a control solution for 1 hour, then serially diluted to drug concentrations between $10^1$ to $10^{-4}$ µg/ml as described in Example 16. Addition of the serially diluted virus suspensions gave the plaque counts, measured in duplicate, shown in Table 9. The "X" symbol in the table indicates plaques too numerous to count. The results of the study demonstrate that inhibition of HSV infection by KY compounds is due, at least in part, to binding of drug to HSV particles. Further, complete virus inhibition was seen at drug final drug concentration of $10^{-2}$ to $10^{-4}$ µg/ml (which are much lower than those needed to inhibit HSV in Vero cell culture). It can be concluded that the drug-binding/inactivation of the virus is effectively irreversible, i.e., not reversed by high dilution effects.

TABLE 9

| KY Compounds | Initial Viral Input (pfu/cell) | Plaque Number after Serial 10-time Dilutions | | | | | |
|---|---|---|---|---|---|---|---|
| | | 1 | $10^1$ | $10^2$ | $10^3$ | $10^4$ | $10^5$ |
| Control (media only) | 0.3 | XX | XX | XX | 50, 41 | 9, 4 | 0, 0 |
| | 3 | XX | XX | XX | XX | 38, 49 | 8, 4 |
| KY 1 (10 µg/ml) | 0.3 | 3, 2 | 0, 0 | 0, 0 | 0, 0 | 0, 0 | 0, 0 |
| | 3 | 2, 2 | 2, 1 | 17, 16 | 5, 2 | 0, 0 | 0, 0 |
| KY 217 (10 µg/ml) | 0.3 | 2, 8 | 3, 3 | 0, 0 | 0, 0 | 0, 0 | 0, 0 |
| | 3 | X, X | X, X | 6, 0 | 5, 0 | 0, 0 | 0, 0 |

Figure 17:
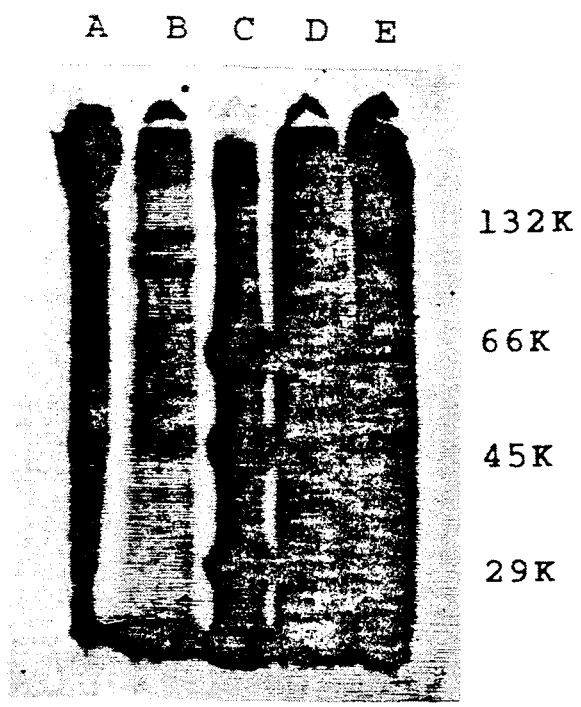
FIG. 17 shows SDS-PAGE autoradiograms of HSV-1 proteins in the presence (lane A) and absence (lane B) of mercaptoethanol, and of HSV-2 proteins in the presence (lane C) and absence (lane D) of mercaptoethanol, all with bound radiolabeled KY-1, and stained marker proteins (lane E)

In a fourth study (Example 17), the binding of radiolabeled KY-1 compound to HSV-1 and HSV-2 viral proteins was examined. After compound binding, virus proteins were fractionated by sodium dodecyl sulfate polyacrylamide gel electrophoresis (SDS-PAGE), and the gel patterns developed by autoradiography. In FIG. 17, lanes A and B in the figure are autoradiographs of HSV-1 proteins in the presence (lane B) and absence (lane B) of mercaptoethanol, and lanes C and D, analogous patterns for HSV-2 proteins. The lane at the right contains the molecular weight markers, as indicated. The major bands of drug binding in HSV-1 have molecular weights, as determined from SDS-PAGE, of 45, 66, and about 130 kilodaltons. The major bands of drug binding in HSV-2 have similar molecular weights. The major bands which show KY binding correspond in molecular weight, to HSV glycoproteins gD, gB, and gC.

In a fifth study, graded topical doses of Y-1 were administered to previously HSV-1-infected corneal regions in rabbits, as described in Example 10. Clinical slit lamp biomicroscopy was used to assess disease severity as measured by average epithelial disease involvement, conjunctivitis rating, iritis rating, and stromal disease.

By day 7 PI, the severity of the epithelial disease had peaked, as observed in placebo treated animals. Conjunctivitis, iritis and stromal disease parameters also progressed throughout the study.

In all four assessments of ocular infection, drug treatment resulted in less severe infection as compared to placebo treatment. All concentrations of Y-1 were effective in reducing the development of HSV-1 induced ocular disease. Therapy with all concentrations of Y-1 were statistically different from each other.

A topical concentration of 12.5 µg/50 µl was the most effective ocular therapy. The epithelial disease scores decreased through day 6 PI and rebounded slightly on day 7 PI. Compared to the other two Y-1 therapies, this concentration was effective in reducing the development of HSV-1 disease in the eye and was associated with only mild conjunctival, iris, and stromal disease development parameters. A higher concentration (18.75 µg/50 µl) was also effective in reducing the development of corneal epithelial HSV-1-induced disease. However, this concentration of Y-1 appeared to be somewhat toxic to the corneal epithelial surface and to the conjunctive, iris and stroma. This toxicity was evidenced as an increase in all disease parameters on days 6 and 7 PI.

In another study, viral titers were determined by plaque reduction and multiple regression analysis, as described in Example 10. In the tear film study, a marked reduction of viral titer was observed in all animals given topical doses of Y-1, and this reduction appeared dose-dependent, although no difference was seen at the highest doses (12.5 and 18.75 μg/50 μl). A dose-dependent reduction in viral titer was observed in the scrapings taken on day 7.

Based upon these studies, dose efficacy/range was generated. The optimal concentration of compound appeared to be 12.5 μg/50 μl in this study.

Effect on Non-Enveloped Viruses

The ability of KY compounds to inhibit cell infection by a rhinovirus and adenoviruses 5 and 7 which are non-enveloped viruses, was similarly studied. Vero cells ($10^5$) were infected with a rhinovirus in the presence of KY-1, at concentrations ranging between 1–100 μg. Twenty-four hours after virus infection, the cells were examined for cytopathic effect, evidencing viral infection. No reduction in cell clumping was observed at any of the KY drug concentrations tested.

Vero cells were infected with adenovirus in the presence of KY-1, also at concentrations ranging between 1–100 μg, and twenty-four hours after virus infection, the cells were examined for cytopathic effect. No reduction in cell clumping was observed at any of the KY-1 drug concentrations.

In summary, a broad range of macrocyclic compounds are effective inhibitors of cell infection by each of the several enveloped viruses which were studied. Binding studies carried out in particular with respect to HSV viruses indicate that the anti-viral activity of the compounds is dependent on binding to virus envelope components, which in turn inhibits virus attachment to infectable cells. The apparent inability of the compounds to inhibit infection of non-enveloped viruses is consistent with this mechanism.

Method of Treatment

In the method of the invention, an aryl macrocyclic compound of the type described in Section II is administered to the site of a viral infection, to inhibit viral infection of host cells. As seen above, the inhibitory effect of the compound is due, at least in part, to the ability of the compound to bind to the infecting virus and block its attachment to infectable host cells.

The main routes of drug delivery, in the treatment method are intravenous, oral, and topical, as detailed below. Other drug-administration methods, such as subcutaneous injection or via inhalation, which are effective to deliver the drug to a target site or to introduce the drug into the bloodstream, are also contemplated. These methods of drug administration are discussed in more detail below.

The dosage which is administered is a pharmaceutically effective dose, defined as a dose effective to inhibit viral infection of host cells. As seen above, compound doses in the range 1–50 μg/ml are generally effective in inhibiting viral infection of cells. Thus, for many applications, an effective dose would be one which produces a concentration of compound in this range at the site of infection. For topical administration, a composition containing between 1–5% or more aryl macrocyclic compound is suitable.

One of the considerations in the treatment method, particularly when the drug is administered for action primarily in the bloodstream, is systemic side effects. Studies conducted in support of the present invention, and reported in co-owned patent application for "Anti-Coagulant Composition and Method", is that certain forms of the macrocyclic compounds show anti-coagulant activity after oral and intravenous administration. The general conclusions from these studies are:

First, highest anti-coagulant activity appears to be associated with particular features of the macrocyclic compounds. Therefore, the compound which is selected for anti-viral inhibition should be one designed to have a high anti-viral/anti-coagulant activity ratio. Drug design considerations which favor a high anti-viral/anti-coagulant ratio are discussed in Section V below.

Secondly, the anticoagulant effect of macrocyclic compounds in the bloodstream can be effectively blocked by administering a polycationic compound, such as protamine sulfate, to produce by intravenous administration. The protamine administration is timed to correspond to highest blood levels of the aryl macrocyclic compounds. In a typical method, a dose of protamine equivalent to about 1 mg per 100 heparin anticoagulant units is administered intravenously simultaneously with IV administration of the macrocyclic compound, or 1–2 hours after oral administration of the macrocyclic drug. It is generally recommended that protamine be infused slowly (i.e., not more than a total of 50 mg/10 minutes). Therefore in the case of simultaneous administration of macrocyclic compound, the rate of co-infusion of the two compounds would be adjusted such that the protamine sulfate was not introduced to the subject at a rate exceeding 50 mg/10 minutes.

Treatment By Intravenous Administration

Studies on the pharmacokinetics and efficacy of intravenously administered macrocyclic compounds of the type described above are discussed in the above-cited parent application for "Treatment for Herpes Simplex Virus". Briefly, it was shown that a macrocyclic compound of the type used in the method, when administered intravenously, (a) is cleared relatively slowly from the bloodstream ($t_{\frac{1}{2}}$=approx. 5–8 hours), (b) is present predominantly in free form, and (c) retains activity in the bloodstream for inhibiting viral (HSV) infection.

Topical Drug Administration

In another treatment method, for inhibiting HSV lesions on an exposed region of a subject, an inhibitory KY compound was contacted with HSV virus by applying the compound to the exposed region of the subject. Female guinea pigs were infected intravaginally with HSV-2, then treated topically three times daily beginning 6 hours or 48 hours after inoculation with HSV-2, as described in Example 13. Animal groups included control animals (no treatment following virus inoculation), placebo (vehicle treatment), KY-1 in vehicle, or acyclovir. Swabs of vaginal secretion were obtained and assayed for viral activity by a standard CPE assay. The severity of genital lesions was scored on a 0–5+ scale through the period of primary infection (21 days).

Three to four days after HSV-2 inoculation, vesicular lesions appeared on the external genital skin. Lesions progressed to an ulcerative stage by days 7–8 and gradually healed by days 15–21. The effect of topical treatment with the KY-1 preparations on lesion development and severity is shown in Table 10. The group treated with placebo at +6h had a significantly increased lesion score-day AUC (P <0.05); however, mean peak lesion scores were not different when compared to the untreated control group. Lesion development as determined by both AUC values and mean peak lesion scores was significantly reduced by treatment with 5% KY-1 when given at 6h after infection compared to the placebo (P <0.001). Treatment with 1% KY-1 significantly reduced the AUC at +6h (P <0.01) but not mean peak lesion scores.

TABLE 10

| Treatment | Lesion Score Area Under Curve | P-Value | Mean Peak Lesion Score | P-Value |
|---|---|---|---|---|
| Control | 37.0 | — | 3.6 | — |
| Placebo + 6 h | 47.0 | <0.05 | 3.9 | NS |
| Placebo + 48 h | 42.8 | NS | 3.6 | NS |
| KY 5% + 6 hr | 3.8 | <0.001 | 0.8 | <0.001 |
| KY 5% + 48 h | 45.7 | NS | 3.7 | NS |
| KY 1% + 6 h | 30.8 | <0.01 | 2.9 | NS |
| KY 1% + 48 h | 46.6 | NS | 4.3 | NS |
| ACV 5% + 6 h | 2.7 | <0.001 | 0.6 | <0.001 |
| ACV 5% + 48 h | 45.8 | NS | 3.8 | NS |

No sign of any skin irritation from any of the formulations was observed. Throughout the treatment period, the genital skin remained normal in appearance; no redness or swelling was observed. The guinea pigs also remained normal and healthy in appearance throughout the entire study.

In another study using the guinea pig genital model described above, animals were infected with HSV-2, then treated with KY-1 or Y-1 topically at concentrations of 2% or 5% drug. Treatment of animals was initiated 6 or 24 hours post infection, as described in Example 13. Animals were treated and scored daily for severity of infection for 19 days. The effects of topical treatment with KY-1 and Y-1 on infection are tabulated in Table 11 and compared to treatment with 5% acyclovir (ACV).

Treatment with placebo (vehicle only) resulted in significantly worse infection scores than no treatment in this study. Drug treatment with 2% or 6% Y-1, administered 6 hours post infection, resulted in reduced numbers of animals exhibiting lesions, decreased mean lesion scores and decreased peak lesion score, in comparison to placebo treatment. Likewise, treatment with a 6% formulation of either KY-1 or Y-1 or a 2% formulation of KY-1, administered 24 hours post-infection, resulted in reduced numbers of lesion bearing animals and reduced severity of lesions.

TABLE 11

Effect of Topical KY-1 and Y-1 on HSV-2 Genital Lesions

| Treatment | Time | N | % Animals with Lesions | Lesion Score (AUC) | Mean Peak |
|---|---|---|---|---|---|
| None | — | 9 | 66.7 | 9.1 | 1.3 |
| Placebo | 6 h | 10 | 100 | 29.0 | 3.0 |
| Y-1 (2%) | 6 h | 9 | 66.7 | 16.9 | 1.8 |
| Y-1 (6%) | 6 h | 10 | 30 | 8.1 | 1.2 |
| Placebo | 24 h | 10 | 100 | 22.3 | 2.7 |
| Y-1 (2%) | 24 h | 10 | 60 | 22.0 | 2.3 |
| Y-1 (6%) | 24 h | 10 | 40 | 14.7 | 1.8 |
| KY-1 (2%) | 24 h | 10 | 70 | 16.2 | 2.2 |
| KY-1 (6%) | 24 h | 10 | 50 | 17.5 | 1.7 |
| ACV (5%) | 24 h | 8 | 37.5 | 11.7 | 1.5 |

Oral Drug Administration

Studies conducted in support of the present invention have shown that a macrocyclic drug of the type used in the invention is available in the plasma for a period from about 0.5 hrs. after oral administration (e.g., by gavage), with a peak at about 2-4 hours. The period of effective drug concentration in the bloodstream is roughly between 4 and 18 hours after IV administration. The relatively short distribution volume halflife of the drug, reflecting distribution to extracorporeal body compartments when the compound is administered intravenously, is generally advantageous in the case where drug is one which shows anti-coagulant side effects, since the concentration of compound in the bloodstream can be more closely titrated.

Drug-Treatment Compositions

In one preferred class of compounds, for use in a treatment method by parenteral or oral administration, the naphthalene-ring $R_2$ positions and the phenyl-ring $R_2$ position in the compounds illustrated above is an alkyl sulfinate or a sulfonamide of the form $SO_2NHR$, where NHR is $NH_2$ or an amino acid.

The alkyl sulfinate may act as a prodrug, in that the ester sulfonyl ester linkage may be cleaved by esterase enzymes in the body, to release an active sulfonate compound. In addition, in vitro studies in anti-viral activity, reported above, show that the methyl sulfinate compound itself is is active against HIV viral infection.

The amino acyl sulfonamide compounds, e.g., KY-376, have been shown to have relatively high anti-viral activity in vitro. In addition, these compounds can be readily modified, by selection of a suitable amino acid, to produce desired solubility and charge properties. For example, the sulfonamide of aspartic acid will carry two charged carboxyl groups, whereas the sulfonamide of a basic amino acid, such as lysine, will carry both a positive and negative charge. The amino acid may be further derivatized at its C-terminus, to produce, for example, a neutral C-terminal ester group.

The following examples illustrate methods of preparing tetrameric macrocyclic compounds, in accordance with the invention, and the use in inhibiting cell infection by enveloped viruses. The examples are intended to illustrate but not limit the scope of the invention.

MATERIALS

All chemical reagents were obtained from Aldrich Chemical Co., or from other commercial sources.

EXAMPLE 1

Preparation of Naphthalene Macrocyclic Compounds

A. KY-1 ($R_1$=OH, $R_2$=$SO_3Na$, $R_3$=H, $R_4$=>$CH_2$)

To a 41 mM aqueous solution (50 ml) of disodium chromotropic acid, 15 ml of 37% formaldehyde was added, giving a final molar ratio of 5:1 formaldehyde:chromotropic acid. The mixture was reacted with stirring in a stoppered flask at room temperature for 1 week. The resulting dark red solution (70 ml) was filtered under vacuum, and the filtrate, after being concentrated was precipitated by adding 200 ml of acetonitrile. The precipitated product was collected by filtration and taken to dryness under vacuum. The yield of KY-1 was 95%. The compound was characterized as follows:

Melting point (M.P.)>300° C.;

HPLC in $CH_3CN/MeOH/H_2O/TFA$: 14'48" single broad peak;

(IR/KBR)=3425 (OH), 1638 (Ar), 1181, 1044 ($SO_3$) $CM^{-1}$;

UV ($H_2O$) 238.0, 358.5 nm

Mol Weight: 1505 (M+1) by mass spectroscopy;

H$^1$ NMR(CD$_3$OD), chemical on the δ scale: 5.20 (CH$_2$, 8.01 (ArH) ppm;

C$^{13}$ NMR (D$_2$O), chemical shifts on the δ scale: 27.19, 120.18, 121.69, 122–06, 122–67, 133–30, 142.97, 154.42 and 181 ppm.

Analysis: (C$_{22}$H$_{10}$O$_{16}$S$_4$Na$_4$)$_2$×6 H20 or (C$_{22}$H$_{11}$O$_{16}$S$_4$Na$_4$)$_2$×5 H$_2$O Found: C 33.17, H 2.54, Na 11.93

Calculated: C 32.75, H 2.23, Na 11.41; C 33.16, H 2.13, Na 11.56.

B. KY-3 (R$_1$=OH, R$_2$=SO$_2$NH$_2$, R$_3$=H, R$_4$=—CH$_2$—)

KY-1 (2 mM) was treated with 5 ml chlorosulfonic acid and the mixture was stirred at 50° C. for one-half hour. The resultant mixture was added to 20 g of crushed ice to precipitate the crude chloride product, which was collected by filtration and then washed with ether.

The crude chloride product was dissolved in 100 ml of 25% ammonium water solution and allowed to react for 2 hours at room temperature. The mixture was concentrated in vacuo and the remaining oil was dissolved in a small amount of water and filtered. The product was precipitated by adding acetonitrile to the filtrate and collected by filtration and washing with acetonitrile. The compound was characterized as follows:

Melting point (M.P.)>300° C.;

Mass spec: 1452 (M-7NH$_2$);.

HPLC in CH$_3$CN/MeOH/H$_2$O/TFA: 11'46" single peak;

(IR/KBR)=3430 (OH) 3187, 1686 (NH$_2$) 1637 (Ar), 1211, 1110, 1044 (SO$_3$) cm$^{-1}$;

UV (H$_2$O) 246 nm;

H$^1$ NMR (D$_2$O), chemical shifts on the δ scale: 5.15 (CH$_2$) 7.5–8.2 (ArH) ppm;

Analysis: (C$_{44}$H$_{40}$O$_{26}$S$_{10}$N$_{12}$Na$_4$) −16H$_2$O

Found: C 28.62, H 3.93, N 8.82, S 17.17, Na 5.44;

Calculated: C 28.51, H 3.89, N 9.07, S 17.28, Na 4.97;

C. KY-42 (R$_1$=OH, R$_2$=SO$_3$Na, R$_3$=H, R$_4$=>CHCOOH)

Chromotropic acid, disodium (10 mM) in 50 ml water was mixed with glyoxylic acid (10.0 mM, in 5 ml water) and 10 ml of 37% hydrogen chloride at room temperature. The mixture was boiled for 8 hours and the color of the solution turned to dark red. The resultant solution was added to 50 ml of water and filtered. The filtrate was concentrated and ethanol was added to precipitate the product of KY-42. The yield was 87%. The compound was characterized as follows:

Melting point (M.P.)>30° C.;

Mass spec: 1623 (M-3H$_2$O).

HPLC in CH$_3$CN/MeOH/H$_2$O/TFA: 10'36" single peak;

(IR/KBR)=3452 (OH), 1801, 1719 (Co), 1638 (Ar), 1206, 1050 (SO$_3$) cm$^{-1}$;

UV (H$_2$O): 238.0, 351.5, 520 nm; H$^1$ NMR (D$_2$O), chemical shifts on the δ scale: 7.10 (CHCO$_2$H) 8.00 (ArH) ppm;

C$^{13}$ NMR (D$_2$O), chemical shifts on the δ scale: 116.04, 118.90, 120.94, 121.27, 122.30, 124.30, 124.68, 126.60, 128.37, 136.48, 136.71, 140.50, 143.93, 144.26, 145.75, 152.01, 154.33, 156.01, 156.67;

Analysis: (C$_{48}$H$_4$O$_{40}$S$_8$Na$_8$)$_4$−4H$_2$O

Found: C 32.74, H 2.50;

Calculated: C 32.58, H 2.71;

D. KY-123 (R$_1$=OH, R$_2$=SO$_2$Na, R$_3$=H, R$_4$=>CH$_2$)

KY-1 (2 mM) was treated with 5 ml chlorosulfonic acid and the mixture was stirred at 50° C. for one-half hour. The resultant mixture was added to 50 g of crushed ice to precipitate the product which was collected by filtration and then washed with ether. The crude sulfonyl chloride product was treated with sodium sulfite (20 Mm) in 4 ml water. The reaction mixture was kept slightly alkaline by addition at intervals of small portions of 50% NAOH for 2 days. After solvent removal, ethanol was added to precipitate the product, which was acidified by addition of 50% H$_2$SO$_4$, followed by addition of ethanol to precipitate sodium sulfate. The ethanol phase was mixed with ether (1:2, v/v) to precipitate the desired product. Product yield was 39%.

E. KY-147 (R$_1$=OH, R$_2$=SO$_2$NHCH$_3$, R$_3$=H, R$_4$=>CH$_2$)

N-methyl chromotropic acid chloride was formed by reacting chromotropic acid (disodium salt) with thionylchloride in the presence of DMF. The reaction was carried out with stirring at 80° C. for 4 hours. After removal of solvent and excess of thionylchloride in vacuo, ether was added to precipitate the chromotropic acid chloride which was subsequently collected by filtration and washed with ether. The crude product was added to 20 ml of methylamine and stirred for 2 hours. After removal of all solvent from the resultant substance, the residue was dissolved in a 200 ml of cold methanol and filtered. The filtrate was added with acetonitrile to precipitate the product chromotropic acid methyl sulfonamide. Yield 56%.

The chromotropic acid methyl sulfonamide (2 mm) in 3 ml water was reacted with 37% formaldehyde (1 ml) at room temperature for one week. Acetonitrile was added to precipitate the product which was collected by filtration and washed by acetonitrile. Yield was 85%.

F. KY-151 (R$_1$=OCH$_3$, R$_2$=SO$_3$Na, R$_3$=H, R$_4$=>CH$_2$)

KY-1 (50 mM) was dissolved in 80 ml of NAOH water solution (0.2M NAOH) and heated to 50° C., dimethylsulfate (0.2M) was added slowly for 1 hour. The mixture was continuously stirred for another 2 hours and left at room temperature for 2 days. Saturated NaCl solution (100 ml) was added to the resultant substance and filtered. The precipitate was washed with ethanol, acetonitrile and ether sequentially. The dry substance was dissolved in 100 ml of methanol and filtered. The filtrate was concentrated and ether was added to precipitate the methyl ether of KT-1.

G. KY-158 (R$_1$=OH, R$_2$=SO$_2$CH$_3$, R$_3$=H, R$_4$=>CH$_2$)

KY-1 from Example 1A was first treated with thionyl chloride to produce chromotropic acid sulfonyl chloride. This compound was reduced by excess sodium sulfite in the presence of sodium bicarbonate to produce the corresponding sodium sulfonate salt of cyclized chromotropic acid (R$_2$=SO$_2$Na) The sulfonate salt was treated with dimethyl sulfate in the presence of NaHCO$_3$, and worked up as as described in Example 1A. Product yield was about 21%.

H. KY-175 (R$_1$=OH, R$_2$=SO$_3$CH$_3$, R$_3$=H, R$_4$=>CH$_2$)

Chromotropic acid was first treated with thionyl chloride to produce chromotropic acid sulfonyl chloride. This compound was then treated with sodium methoxide in methanol in the presence of sodium salt. The product was worked up as described in Example 1A to form the macrocyclic compound. Product yield was about 29%.

KY-270 ($R_1$=OCOCH$_3$, $R_2$=SO$_3$Na, $R_3$=H, $R_4$=>CH$_2$)

KY-1 from Example 1A (0.66 mmole) was dissolved in 3 ml water containing 0.1 g NAOH. To this was added 1 g acetyl chloride (13 mmole) and the reaction was allowed to proceed at room temperature overnight with stirring. After solvent removal, 25 ml ethanol was added to precipitate the product. The crude product was dissolved in methanol and filtered. The filtrate was allowed to precipitate, giving a 87% yield.

KY-346 ($R_1$=OH, $R_2$=SO$_3$Na, $R_3$=H, $R_4$=—CH$_2$—N (CH$_3$)CH$_2$)

Chromotropic acid disodium salt, was dissolved in 80 ml of water at a concentration of 50 mM with stirring at 50° C. until the solution turned to clear, hexamethylenetetramine (50 mM) was then added to above solution with continuous stirring at the same temperature for additional two hours. At this time, the color of this mixture converted to dark blue. The mixture was allowed to stir at room temperature for 2 days. The resultant dark blue solution was filtered and the filtrate was concentrated, evaporated by flask, which was subsequently treated with 200 ml methanol to precipitate the product KY-346. The yield of KY-346 was 85%. The compound was characterized as follows:

M.P.>300° C.;

HPLC in CH$_3$CN/MeOH/H$_2$O/TFA: 13'07" single peak;

(IR/KBr)=3425 (OH), 1626 (Ar), 1197, 1052 (SO$_3$) cm$^{-1}$;

UV (H$_2$O): 232.0, 377.5 nm

Analysis: (C$_{13}$H$_{11}$O$_8$NS$_2$Na$_2$)$_4$×12 H$_2$O

Found: C 33.17, H 3.13, N 2.75

Calculated: C 33.98, H 3.59, N 2.96.

Molecular weight: 1668 by gel filtration.

EXAMPLE 2

Preparation of Phenyl Macrocyclic Compounds

A. Y-49 ($R_1$=OH, $R_2$=SO$_3$H, $R_4$=—CH$_2$—, n=4)

4-tert-butylcalix(4)arene (10 g) was treated with 200 ml of concentrated H$_2$SO$_4$ at room temperature for 0.5 hour and then at 75°–85° C. oil bath for another 4 hours. The reaction was completed when no water-insoluble material was detected. The resultant oil was dropped into 500 g of crushed ice and the solution was filtered by reduced pressure. After the water removed away from the filtrate, acetonitrile (500 ml) was added to the residual and allowed to stand for 4 hours to precipitate the crude product which was then collected by filtration and washed with acetonitrile, ethyl acetate and ether. Yield 8 g (73%). The pure product was furnished by recrystallization of the crude compound with methanol-ether or methanol-acetonitrile system. The single crystal compound was also found in the recrystallization process.

Similar methods were used in the synthesis of Y-77 ($R_1$=OH, $R_3$=SO$_3$H, $R_4$=—CH$_2$—, n=6) and Y-1 ($R_1$=OH, $R_3$=SO$_3$H, $R_4$=—CH$_2$—, n=8).

B. KY-225 ($R_1$=—OH, =O), $R_2$=SO$_3$H, $R_4$=>CH$_2$, ≧CH, n=4)

4-tert-Butylcalix(4)arene (1 g) was treated with 10 ml of 95-98% sulfuric acid at room temperature for 0.5 hours then at 160° C. for 5 minutes. After the resultant mixture was cool, the mixture was poured slowly into 100 ml of crushed ice and filtrated. The solution was evaporated and the residual was added with 300 ml acetonitrile to produce great amount of precipitate which was collected by filtration and washed with acetonitrile. The crude product was dissolved in 20 ml methanol and the product was precipitated by addition of diethyl ether. Yield 84%.

Similar methods were used in the synthesis of Y-48 ($R_1$=—OH or =O, $R_3$=SO$_2$H, $R_4$=—CH$_2$—, n=6) and Y-226 ($R_1$=—OH or =O, $R_2$=SO$_3$H, $R_4$=—CH$_2$—, n=8).

C. O-Acetylate of Y-1 ($R_1$=—OCOCH$_3$, $R_2$=SO$_3$Na, $R_4$=>CH$_2$, n=8)

Under nitrogen, Y-1 (0.4 g) was refluxed in a stirring mixture of NaOAc (305 mg) and acetic anhydride (20 ml) for 3 days. After cooling to room temperature, the suspension was filtered. The solid was washed three times with ether (25 ml) and dried in vacuo. The resulting solid was sonicated in a mixture of MEOH (50 ml) and activated charcoal (150 mg), filtered, and the black precipitate was washed twice with MEOH (10 ml). The filtrate was concentrated in vacuo. The resulting residue was recrystallized from MeOH/acetonitrile mixture. The product (240 mg) was obtained after filtration and lyophilization.

$^{13}$CNMR (D$_2$O, δ): 173.9, 151.6, 144.1, 135.6, 130.1, 34.2, and 22.4.

D. Y-78 ($R_1$= —OH, $R_2$=SO$_2$NH$_2$, $R_4$= >CH$_2$, n=8)

Under nitrogen, Y-1 (1 g) is heated at 60°-70° C. with chlorosulfonic acid (20 ml) for 1 hour. After cooling to room temperature, the oily material is poured into ice water, and the precipitate is filtered. After washing the precipitate with cold water, the crude product is dissolved in 100 ml of 25% ammonium water solution and allowed to react for 2 hours at room temperature. The mixture is concentrated in vacuo and the remaining oil is dissolved in a small amount of water and filtered. The product is precipitated by adding acetonitrile to the filtrate and collected by filtration and washing with acetonitrile.

E. Glycyl sulfonamide of Y-1 ($R_1$= —OH, $R_2$=SO$_2$NHCH$_2$CO$_2$H, $R_4$= >CH$_2$, n=8)

Under nitrogen, Y-1 (1 g) is heated at 60°-70° C. with chlorosulfonic acid (20 ml) for 1 hour. After cooling to room temperature, the oily material is poured into ice water, and the precipitate is filtered. After washing the precipitate with cold water, the material is added to 50 ml of solution containing 5.7 g glycine and 2.1 g NAOH, and stirred for 2 hours at room temperature. After removal of all solvent from the resultant substance, the residue is dissolved in a 200 ml of cold methanol and filtered. The filtrate is added with acetonitrile to precipitate the product.

F. Acetyl-Bridged Y-49 ($R_1$= —OH, $R_2$=SO$_3$H, $R_4$= —CHCO$_2$H—, n=4)

4.3 g of p-hydroxybenzenesulfonic acid was treated with g gram of glyoxylic acid in 30 ml 18% conc. HCl for 2 hours at 100° C. After the reaction product was dried under reduced pressure, 50 ml of methanol was added and insoluble impurities were removed by filtration. The product was precipitated from the filtrate by addition of ether then collected by filtration and dried in vacuo.

G. Toluene Sulfonyl Ester of Y-49 ($R_1$= —SO$_3$C$_6$H$_4$CH$_3$, $R_2$=SO$_3$H, $R_4$= >CHCO$_2$H, n=4)

Under nitrogen is added toluenesulfonyl chloride (1.9 g) to a suspension of dry sodium carbonate (1.06 g), dry dimethylformamide (10 ml) and Y-49 (0.75 g). After an overnight reflux, the resulting mixture is cooled to room temperature and filtered. The filtrate is diluted with ether to precipitate out the crude product. Recrystallization from acetonitrile/ether solvent provided the product.

H. Carboxylic Acid Derivative of Y-49 ($R_1=$ —$CH_2H$, $R_2=SO_3H$, $R_4=$ >$CHCO_2H$, n=4).

Under nitrogen, trifluoromethanesulfonic anhydride (1.0 ml) is added to ice cold dry dichloromethane solution (10 ml) of 2,6, di-tert-butyl-4-methylpyridine (1.25 g) and 4-tert-butylcalix[4]arene (0.65 g). After overnight stirring at room temperature, the mixture is diluted with pentane (10 ml) and filtered. The filtrate is extracted with ice cold 1N aqueous NAOH solution, ice cold 1N aqueous HCl solution, then saturated aqueous NaCl solution, dried over anhydrous sodium sulfate, filtered through a pad of silica gel and concentrated in vacuo. The residue is dissolved in a mixture of dry diisapropylethylamine (10 ml), trimethylsilyl cyanide (0.5 ml) and palladium tetrakis-triphenylphosphine (20 mg). After an overnight reflux under nitrogen and then cooling to room temperature, ether (50 ml) was added and the resulting suspension was filtered. After concentration of the filtrate in vacuo and silica gel chromatography (hexane/ethyl acetate eluent), the cyano intermediate is heated at 80° C. with concentrated sulfuric acid (10 ml) for 3 hours, diluted with water (10 ml) and refluxed overnight. After cooling to room temperature, the resulting mix is added to charcoal (0.5 g) and ice (50 g). After filtration, the resulting filtrate is concentrated in vacuo to ca 15 ml in volume and the resulting solid was filtered. The solid is dissolved in a minimal amount of methanol and precipitated out by adding ether. Final purification by reverse phase C18 chromatography (methanol/water eluent) provide the product.

I. Methyl Ether of Y-1 ($R_1=OMe$, $R_3=SO_3Na$, $R_4=$ >$CH_2$, n=8).

Iodomethane (0.58 ml) was added to a heated (50° C.) mixture of Y-1 (447 mg), NAOH (6N in water, 1.53 ml), and dimethylsulfoxide (9 ml) for 20 hours. The resulting mix was added dropwise into stirring absolute ethanol (100 ml). The resulting suspension was centrifuged (9,000 rpm, 20 minutes), and then the supernatant was removed. Twice, the resulting solid was dissolved in water (6 ml), and the resulting solution was treated as above with ethanol, centrifuged, and the supernatant removed. The remaining solid was lyophilized to yield the product (420 mg).

$^{13}CNMR$ ($D_2O$, δ): 161.2, 140.9, 137.6, 129.5, 63.6, and 33.5.

EXAMPLE 3

Preparation of Aryl-Bridged Macrocyclic Compound

Chromotropic acid, disodium (10 g) in 55 ml of water was treated with 22 ml of 30 ml 37% HCl. To this solution, 1,2-benzenedimethanol (5 g) in 55 ml of acetic acid was added and this reaction was carried at reflex for 6 hours. After filtration of the resultant mixture, acetonitrile (500 ml) was added to precipitate the crude product and collected it by filtration. The crude compound was further purified by column chromatographic purification on LH-20 resin and elution with ethanol.

EXAMPLE 4

Cytotoxicity in Proliferating Cells

A panel of human cell lines was used to check the toxicity of the drugs, including: KB (nasopharyngeal carcinoma), HeLaS$_3$ (cervical epithelial carcinoma), PLC (hepatocarcinoma), HepG$_2$ (human hepatocarcinoma) HepG$_2$T$_{14}$ (hepatocarcinoma transfected with HBV), WI38 (normal human lung fibroblast), BT549 (breast cancer), SW480 (breast cancer), and A549 (lung cancer).

$5 \times 10^4$ cells were plated in each well of a 24 well multi-dish in 1 ml of RPMI-1640 containing 5% FCS and P/S. On the second day after plating, one of the fifty test compounds given in Table 3 was added to the cells, at concentrations between 1–100 μg/ml. Three days later, the medium was removed and the cells were stained with Commassie Blue in 40% methanol and 7% acetic acid. The results are discussed in Section II above.

EXAMPLE 5

Inhibition of HSV Activity: Cytopathic Effect

Vero cells were maintained in RPMI-1640 medium supplemented with 5% fetal calf serum, 100 Units of penicillin per ml and 100 μg of streptomycin per ml at 37° C. in a humidified incubator containing 7% $CO_2$. The HSV strains HSV-1 (Kos-1) and HSV-2 (333) were used.

$1 \times 10^5$ Vero cells were plated in each well of a 96 well microtitre plate in 0.2 ml RPMI-1640 medium containing 5% FCS and 0.1% methyl cellulose (15 cps). After overnight incubation, and cell doubling, the medium was aspirated and replaced with 100 ml of the same medium containing 2% FCS, and 50 μl control or drug solution to a final drug concentration of 10 μg/ml and 50 μl virus, containing about 3 PFU/cell, i.e., $6 \times 10^5$ PFU/well, of HSV-1 or HSV-2.

The cells were cultured for 24 hours at 37° C., at which time cytopathic effects are clearly visible. In the absence of viral infection, the cells form an even monolayer of fibroblast cells. With viral infection, the cells form a suspension of round cells, followed by cell clumping, whose appearance is easily distinguishable from normal fibroblast cells. If no detectable cytopathic effect was produced, the test was repeated with 10 μg/ml. A parallel set of cells without virus inoculation were done as a control for cytotoxicity to Vero cells.

Table 1 above shows the structures of the compounds which were tested, and Table 3, column 2, the compounds which protected the cells from cytopathic effect (+).

EXAMPLE 6

Inhibition of HSV Activity: Plaque Reduction

Vero cells were maintained in RPMI-1640 medium supplemented with 5% fetal calf serum, as in Example 5. $4 \times 10^5$ Vero cells were plated in a 24-well plate, in 1 ml RPMI-1640 medium containing 5% FCS and 0.1% methyl cellulose (15 cps). After overnight incubation, and cell doubling, the medium was aspirated and replaced with 100 μl of the same medium containing 2% FCS, which contained 50 μl control or drug solution to a final drug concentration of 0.25, 2.5, 5, 10, or 20 μg/ml and 50 μl virus, containing about $1 \times 10^3$ PFU/ml, i.e., 50 PFU/well, of HSV-1 or HSV-2, as in Example 5.

After 2 hrs. at 37° absorption the virus and the drugs were removed and the cells were washed with PBS and 0.5 ml of 1% methylcellulose (4K cps) in RPMI-1640+2% FCS +penicillin/streptomycin (P/S) was added. Two days later, the media were removed. The cells were stained with 0.8% crystal violet in 50% ethanol. The plaques formed were counted and the percentage of inhibition was calculated by dividing by the plaques formed in control. $ED_{50}$ values, indicating the concentration of drug needed to produce 50% inhibition of viral plaques, were calculated assuming a linear dose response for viral plaque inhibition. The calculated $IC_{50}$ values are given in Tables 3 and 4 above.

EXAMPLE 7

Inhibition of HSV Activity: Viral Yield Inhibition $1 \times 10^6$ HeLa $S_3$ were plated in 25 T flasks in 5 ml RPMI-1640 +5% FCS +P/S. 24 hours later, the medium was aspirated and replaced with $6 \times 10^6$ PFU HSV-1 or HSV-2, and serial dilutions of selected KY compounds, at 10, 5, 2.5, 1.25, and 0.625 µg/ml drug. After growth at 37° C. for 24 hours in 2 ml of RPMI-1640 containing 2% FCS and P/S, the cells were frozen at $-70°$ C. until the time for titration. The cells were freeze/thawed 3 times to release virus from the cells, and serially diluted 10 fold.

$1 \times 10^5$ Vero cells were plated in each well of 24 well multi-dish in 1 ml RPMI-1640 +5% FCS +P/S +0.1% methylcellulose (15 cps). On the second day, after removal of the medium, the 10 fold serially diluted virus in 100 µl was added in duplicate. After 2 hours incubation at 37° C., the virus was removed and 0.5 ml methycellulose (4K cps) in RPMI-1640 and 2% FCS +P/S was added. Two days later, the medium was removed. The cells were stained in 0.8% crystal violet in 50% ethanol. The plaques formed were counted and the titer was calculated from the fold of dilutions.

The reduction in virus yield, as a function of KY compound concentration, is seen in FIGS. 14A and 14B for KY-1 and KY-2.

EXAMPLE 8

Activity Against Drug-Resistant Strains of HSV-1 and HSV-2

The following strains of HSV-1 and HSV-2 virus were used: KOS, a wild type HSV-1 virus; KOS (PMEA) and KOS (PFA), both drug-resistant HSV-1 viruses having a DNA polymerase mutation; 333, a wild type HSV-2 HSV-2 virus, and 333 (DHPG), a drug-resistant HSV-2 virus having a thymidine kinase mutation.

Inhibition of viral yield was by KY-1, acyclovir (ACV), DHPG, PFA, and PMEA was examined in each of the five HSV strains substantially as described in Example 7. Briefly, Hela $S_3$ were plated in 25 T flasks in culture, and 24 hours later, the medium was aspirated and replaced with $6 \times 10^6$ PFU of the selected HSV strain, and serial dilutions of KY-1, ACV, DHGP, PFA, and PMEA. After growth at 37° C. for 24 hours in 2 ml of RPMI-1640 containing 2% FCS and penicillin and streptomycin (P/S), the cells were frozen at $-70°$ C. until the time for titration. The cells were freeze/thawed 3 times to release virus from the cells, serially diluted 10 fold, and the serial dilutions were added to Vero cells in culture. After 2 hours incubation at 37° C. the virus was removed and 0.5 ml methycellulose (4K cps) in RPMI-1640 and 2% FCS +P/S was added. Two days later, the medium was removed. The cells were stained in 0.8% crystal violet in 50% ethanol. The plaques formed were counted and the titer was calculated from the fold of dilutions. From the drug dose response, the concentration of each drug required to effect a 90% inhibition of virus yield, the $IC_{90}$ concentration was determined. These values are shown in Table 5 above.

EXAMPLE 9

Inhibition of RSV Activity

Assays to assess the antiviral activity of KY- and Y-compounds in tissue culture were performed in 96-well flat-bottom tissue culture plates (Falcon 307), using conditions similar to those used in the cytotoxicity assays described above. In these assays, compound was tested in quadruplicate by serially diluting the compound in 2% FCS-MEM using serial two-fold dilutions (0.05 ml/well). A 0.05 ml volume of the appropriate virus containing approximately 100 median tissue culture infectious doses ($TCID_{50}$) was then added to all wells except those set aside as antiviral and tissue control wells. Next, approximately $3 \times 10^3$ HEp2 cells (0.1 ml) were added to each well. Control wells containing antiviral and no virus (antiviral control), containing virus but no antiviral (virus control), or containing medium without virus or antiviral (tissue control), were included in each test. The challenge virus was then back titrated. All assay plates were incubated at 35° C. for 5 to 7 days in a 5% $CO_2$ incubator. When virus control wells exhibited 70% to 100% CPE including syncytia, all wells were observed. The median efficacious concentration ($IC_{50}$) was calculated after determining the final concentration of antiviral in the last wells in each set of quadruplicate rows exhibiting <50% CPE compared to the CPE in virus control wells. The $ED_{50}$ values calculated for each of the compounds tested are shown in Table 5.

EXAMPLE 10

Activity against HSV virus: Topical activity against in vivo ocular cultures of HSV-1

New Zealand white rabbits were acclimated for a minimum of two days prior to inoculation to allow the animals to accommodate to conditions in the vivarium facility. After the accommodation period, animals received a slit lamp ocular examination to exclude any animals with preexisting anterior segment ocular defects. Animals were bilaterally inoculated topically with an 80 µl drop of Minimal Essential Medium (MEM; Gibco) containing $10^5$ pfu/ml McKrae strain HSV-1; eyes were massaged for 30 seconds. Animals were replaced individually in cages.

On day 4 post inoculation (PI), animals were evaluated by slit lamp microscopy. Corneal epithelial, iris, and conjunctival disease were graded on an increasing scale of severity from 0+ to 4+. After evaluation, animals were divided into 4 groups of 5 animals with matched corneal, stromal and conjunctival involvement. Topical therapy was initiated immediately after animal grouping. Therapy groups included:

Group #1: 5 rabbits, Y-1 topical therapy (6.25 µg/50 µl) 5×/day for 4 days;

Group #2: 5 rabbits, Y-1 topical therapy (12.5 µg/50 µl) 5×/day for 4 days;

Group #3: 5 rabbits, Y-1 topical therapy (18.75 µg/50 µl) 5×/day for 4 days;

Group #4: 5 rabbits, placebo therapy (sterile water) 5×/day for 5 days.

The concentration of Y-1 for the ascending dose tolerance study were based upon the ED90 concentrations determined in the virus yield or CPE assays. Group 1 received topical eyedrop therapy containing 6.25 μg/50 μl [one-half of the ED90 concentration]; Group 2 received eyedrop therapy containing 12.5 μg/50 μl (the ED90 concentration]; Group 3 received eyedrop therapy containing 18.75 μg/50 μl (1.5 times the ED90 concentration]. All Y-1 doses were formulated to contain these concentrations in a volume of 50 μl (a standard eye drop).

Topical therapy with 0–19 μg Y-1 in 50 μl was initiated on day 4 post-inoculation (PI) and continued to day 7 PI. All animals received daily ocular slit lamp evaluations from day 3 through day 7 PI. The ocular HSV-1 induced disease severity was recorded daily.

Eyes of all animals were additionally sampled for the presence of infectious HSV-1 on days 0 (preinoculation), 3, 5, and 7 PI. Briefly, tear film was obtained by swabbing the lower and upper conjunctival sacs and retaining the swab in the nasal fornix for 10 seconds. The swabs were eluted individually in Hank's Buffered Saline (HBSS, Gibco Laboratories). Fifty microliter aliquots of the virus-HBSS eluate was adsorbed onto confluent HFF cell monolayers for 5 minutes. Monolayers were hydrated with Minimal Essential Medium (MEM; Gibco Laboratories), incubated at 37° C. and observed daily for two weeks to detect cytopathology consistent with HSV infection (HSV CPE). Cultures not exhibiting HSV CPE were blind passaged to confirm negativity.

On day 7 PI (sacrifice), the corneal epithelium was scraped from the eyes and HSV was recovered on HFF cell monolayers. Corneal epithelial co-cultures were evaluated daily by inverted light microscopy. Cultures not exhibiting HSV CPE were blind passaged to confirm negativity.

Clinical efficacy of the three Y-1 concentrations used in single-agent therapies were compared to placebo therapy. Virus recovery during and after topical therapy with the Y-1 formulations were compared to each other and to placebo therapy. The results of these studies are discussed in section III.A above, "Mechanism of Viral Infection Inhibition", beginning at paragraph 5.

EXAMPLE 11

Inhibition of Influenza A Activity

The anti-influenza A activity of KY compounds was evaluated as described in Example 9, except that MDCK cells (kidney cell line) was used for infection in vitro by influenza virus (strain A/Taiwan).

EXAMPLE 12

Inhibition of HIV-Induced Cell Fusion

Human $CD_4^+$ indicator cells (VB) and chronically infected $H_9$ cells were maintained in RPMI-1640 medium supplemented with 5% fetal calf serum, 100 Units of penicillin per ml and 100 μg of streptomycin per ml at 37° C. in a humidified incubator containing 7% $CO_2$. The HIV strains that were used were HTLV-III$_B$ and RF-II strains obtained from the National Institutes of Health (Bethesda, Md.).

For the fusion assay, serial dilutions between 1:2 and $1:2^8$ of a selected KY compound, 1 mg/ml in PBS were made in a 96 well round bottom plate. The diluted KY compound was transferred to a 96 well flat-bottom plate. To each well was added 25 μg chronically infected Hg cells (at $2 \times 10^6$, cells/ml), or cells chronically infected with RF-II strain HIV, followed by incubation at 37° C. for 45 minutes. To each well was then added 25 μl VB cells (about $5 \times 10^4$ cells), and the cells and virus isolates were cocultured for 18 hours in a humid 5% $CO_2$ atmosphere. The extent of syncytia formation was scored under phase microscopy, and the concentration which completely inhibited syncytia formation ($ED_{100}$) was recorded. The results are given in Table 7.

EXAMPLE 13

Effect of KY Topical Administration on Genital HSV Infection

A. Virus and Viral Inoculation

The MS strain of HSV-2 was utilized for the experimental animal infection. Female Hartley strain guinea pigs (Charles River Breeding Laboratories, Kingston, N.Y.) weighing 250–300 g were inoculated intravaginally with $2.0 \times 10^5$ plaque-forming units of HSV-2 one hour after being swabbed for removal of vaginal secretions.

B. Treatment of Guinea Pigs

In the first study, groups of 10 guinea pigs were treated topically (0.1 ml intravaginally +0.1 ml on external genital skin) three times daily (approximately every eight hours) for seven days beginning 6h or 48h after inoculation with HSV-2. Groups of three uninfected animals were treated in a similar manner to assess any skin irritation.

In a second study, groups of 8–10 animals were treated three times daily with topical formulations of 2% or 6% KY-1 or Y-1, with treatment beginning either 6 or 24 hours following viral inoculation, as indicated in Table 8B. Formulations of KY-1 or Y-1 were prepared by dissolving the compound in a 1.5% methyl cellulose solution such that final concentration of compound was 2% or 5% (wt/wt). Control animals were given either no treatment (N=10 animals) or treatment with placebo (1.5% methylcellulose solution).

C. Sample Collection and Virus Assays

To determine the effect of treatment on vaginal viral replication, swabs of vaginal secretions were obtained on days 1, 3, 5, 7 and 10 after HSV inoculation, placed in a tube containing 2.0 ml of media, vortexed and frozen at −70° C. until titrated for HSV-2. When all samples were collected, they were thawed, diluted serially and HSV-2 titers determined using rabbit kidney cells in a microtiter CPE assay.

D. Evaluation of Efficacy

To determine the effect of therapy on the development and spread of external genital lesions, lesion severity was scored on a 0–5+ scale through the primary infection period (19–21 days). Lesion score-day areas and virus titer-day areas under the curve, and peak lesion scores and peak virus titers between untreated and placebo-treated or placebo-treated and drug-treated animals were compared using the Mann-Whitney U range sum test. A p-value of 0.05 or less was considered significant. The results are discussed with reference to Tables 10 and 11 in Section IV above.

Animals were scored daily for 19 days following inoculation for presence of lesions and severity of lesions (on a 0–5+ point scale). Lesion scores were tabulated as area under the curve of daily lesion score vs. time (days) and peak lesion score observed. Data are presented in Table 11. A known antiviral agent, acyclovir (ACV) was administered in a 5% formulation to 8 animals as a positive control in the study.

EXAMPLE 14

Inhibition of HSV-1 Binding to Vero Cells

Vero cells were maintained in RPMI-1640 medium, as described in Example 5. After overnight incubation, and cell doubling, the medium was aspirated and replaced with 100 μl of medium containing 2% FCS composed of 50 μl control or drug solution to a final drug concentration of 10 μg/ml and 50 μl virus, containing about 3 PFU/cell, i.e., $6 \times 10^5$ PFU/well, of $H^3$-labeled HSV-1. At time intervals of 5, 30, 60, 120, and 240 minutes, cells were removed from the suspension, washed two times with PBS, and assayed for bound virus (cpm $^3H$). The results are given in FIG. 15, where the control virus binding is indicated by solid circles, and the drug-inhibited binding, by open rectangles.

EXAMPLE 15

Effect of Drug/Virus Exposure on HSV Inhibition

Vero cells were maintained in RPMI-1640 medium, as above. After overnight incubation, and cell doubling, the medium was aspirated and replaced with 100 μl of medium containing 2% FCS. In one group of wells, serial dilutions of KY-1 compound, between 0.625 and 10 μg/ml drug were added in 50 μl, together with 50 μl of HSV-1 virus suspension, $5 \times 10^6$ PFU per well. The cells were incubated for 2 hours at 37° C., then washed with PBS and assayed for number of virus plaques, as in Example 6.

In a second group of cells, serial dilutions of the drug were added to the cells, prior to the addition of the HSV-1 virus, and the cells were incubated for 2 hours at 37° C. in the presence of the virus. After washing the cells to remove free drug, virus suspension was added, $5 \times 10^6$ PFU per well. The cells were incubated for 2 hours at 37° C., then washed with PBS and assayed for number of virus plaques, as in Example 6.

In a third group of cells, 100 μl virus suspension was added to the cells, $5 \times 10^6$ PFU per well, and the cells were incubated for 2 hours at 37° C., then washed with PBS to remove unbound virus. Serial dilutions of KY-1 compound, between 0.625 and 10 μg/ml drug were added to the cells in 100 μl. The cells were incubated for 2 hours at 37° C. in the presence of the drug, then washed with PBS and assayed for number of virus plaques, as above.

The numbers of plaques observed in each of the above treatment methods, expressed as percent of untreated control, are plotted in FIG. 16. The solid circles indicate co-exposure of the cells to drug and virus; the solid squares, preincubation of the cells with drug before addition of virus; and the open squares, preincubation of the cells with virus before addition of drug.

EXAMPLE 16

Inactivation of HSV-1 by KY compounds

Purified HSV-1 was suspended in RPMI-1640 medium (Gibco Laboratories) containing 2% FCS, penicillin and streptomycin. To aliquots of the suspensions were added control, KY-1, or KY-217 solution, to a final drug concentration of 10 μg/ml, and a final virus particle concentration of $6 \times 10^6$ or $6 \times 10^5$ PFU/ml. The suspensions were incubated for 1 hour at 37° C., then diluted serially at 10 fold dilutions to final drug concentrations of 10, $10^0$, $10^{-1}$, $10^{-2}$, $10^{-3}$, and $10^{-4}$ μg/ml drug concentrations. The serially diluted particles were then added to Vero cells for two hours, as in Example 6, and the cells examined for plaques 48 hours later. The number of plaques counted on each of two plates, for each virus and drug concentration, are given in Table 9.

EXAMPLE 17

Binding of KY Compounds to HSV Proteins

A. Binding of KY compound to HSV Proteins

HSV-1 and HSV-2 viral suspensions from above, each at a concentration of about $5 \times 10^7$ CFU/ml, were incubated for 2 hours at 37° C. with $5 \times 10^5$ cpm $^{14}C$-labeled KY-1 (50 μg/ml). Each viral suspension was divided into two aliquots and solubilized with 0.5% sodium dodecyl sulfate (SDS), with or without 1% mercaptoethanol. The four solubilized samples were fractionated on 8.5% polyacrylamide gel, and the gels developed by autoradiography, according to standard procedures. The autoradiographs of the four samples are seen in FIG. 17, where the lanes are HSV-1, with (lane A) and without (lane B) mercaptoethanol, and HSV-2, with (lane D) and without (lane E) mercaptoethanol, with the marker proteins in lane C.

B. Identification of Binding Proteins

HSV-1 and HSV-2 virus suspensions were solubilized with SDS and fractionated on SDS-PAGE as above. Each sample was run in triplicate, corresponding to three groups designated D, B, and C. The gels in each group were analyzed by Western blotting as follows: The gels in groups D, B, and C were first reacted with mouse monoclonal antibody specific against HSV glycoprotein gD, aB, and dC, respectively. The antibodies were obtained from Dr. S. Chatterjee from the University of Alabama. The gels were then incubated with alkaline phosphatase-labeled goat anti-mouse antibody, to label the glycoprotein in each group. The glycoprotein with bound antibody was identified by reaction with $H_2O_2$ in the presence of nitroblue tetrazolium and bromochloroindolephosphate, according to standard methods. The results from this example are discussed in section III.A above, "Mechanism of Viral Infection Inhibition", at paragraph 4.

Although the invention has been described with reference to preferred compounds and method of virus inhibition employing the compounds, it will be appreciated that various modification and changes may be made without departing from the invention.

It is claimed:

1. A method of inhibiting cell infection by a herpesvirus comprising
administering to the site of infection a therapeutically effective dose of a macrocyclic compound which has the form

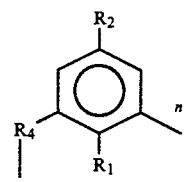

where $R_2$ is a sulfonic acid, sulfonate salt, sulfinic acid, sulfinate salt, alkyl sulfonate, alkyl sulfinate, or a sulfonamide, $R_1$ is OH, =O, an alkyl or aryl ether, ester, or acid, or a mixture thereof, $R_4$ is >CHR" or ≧CR", where R" is H or a carboxylic acid group, and n=4, 6, or 8.

2. The method of claim 1, wherein $R_2$ is an alkyl sulfinate, alkyl sulfonate, or $SO_2NHR$, where NHR is $NH_2$, NHOH or an amino acid.

3. The method of claim 1, wherein some of the $R_1$ groups are =O.

4. The method of claim 1, wherein the compound is administered orally.

5. The method of claim 4, which further includes administering to the subject, a dose of protamine sulfate effective to inhibit anti-coagulant effects of the macrocyclic compound.

6. The method of claim 1, wherein the compound is administered topically.

7. The method of claim 1, wherein the compound is administered intravenously and which further includes administering to the subject, an amount of protamine sulfate effective to inhibit anti-coagulant effects of the mcarocyclic compound.

8. The method of claim 1, wherein n is 6 or 8.

* * * * *